United States Patent
Sato et al.

(10) Patent No.: US 11,668,696 B2
(45) Date of Patent: Jun. 6, 2023

(54) MASK STRUCTURE OPTIMIZATION DEVICE, MASK STRUCTURE OPTIMIZATION METHOD, AND PROGRAM

(71) Applicants: RIKEN, Saitama (JP); ThinkCyte, Inc., Tokyo (JP)

(72) Inventors: Issei Sato, Wako (JP); Masahiro Kazama, Tokyo (JP); Masashi Ugawa, Tokyo (JP); Hiroaki Adachi, Tokyo (JP); Fumiya Shimada, Tokyo (JP)

(73) Assignees: RIKEN; THINKCYTE, INC.

( * ) Notice: Subject to any disclaimer, the term of this patent is extended or adjusted under 35 U.S.C. 154(b) by 0 days.

(21) Appl. No.: 17/706,962

(22) Filed: Mar. 29, 2022

(65) Prior Publication Data

US 2022/0222935 A1   Jul. 14, 2022

Related U.S. Application Data

(62) Division of application No. 16/965,311, filed as application No. PCT/JP2019/003120 on Jan. 30, 2019, now Pat. No. 11,314,994.

(30) Foreign Application Priority Data

Jan. 30, 2018   (JP) ................................. 2018-014150

(51) Int. Cl.
*G06V 10/88*   (2022.01)
*G01N 15/14*   (2006.01)
(Continued)

(52) U.S. Cl.
CPC ......... *G06V 10/88* (2022.01); *G01N 15/1429* (2013.01); *G01N 33/4833* (2013.01);
(Continued)

(58) Field of Classification Search
CPC .... G06V 10/88; G06V 10/507; G06V 20/695; G06V 20/698; G01N 15/1429;
(Continued)

(56) References Cited

U.S. PATENT DOCUMENTS

| | | | |
|---|---|---|---|
| 5,991,433 A | 11/1999 | Osanai et al. | 382/133 |
| 2008/0013816 A1 | 1/2008 | Rimm | |

(Continued)

FOREIGN PATENT DOCUMENTS

| | | |
|---|---|---|
| JP | 09-308619 A | 12/1997 |
| JP | 2008-533440 A | 8/2008 |

(Continued)

OTHER PUBLICATIONS

International Search Report dated Apr. 16, 2019 in corresponding PCT International Application No. PCT/JP2019/003120.

(Continued)

*Primary Examiner* — Casey L Kretzer
(74) *Attorney, Agent, or Firm* — Ostrolenk Faber LLP

(57) ABSTRACT

A mask structure optimization device includes a classification target image size acquisition unit that is configured to acquire a size of a classification target image which is an image including a classification target, a mask size setting unit that is configured to set a size of a mask applied to the classification target image, a brightness detection unit that is configured to detect a brightness of each pixel within the classification target image at a position on an opposite side of the mask from the classification target image, a sum total brightness calculation unit that is configured to calculate the sum total brightness of the each pixel within the classification target image detected by the brightness detection unit, an initial value setting unit that is configured to set an initial value for a mask pattern of the mask, and a movement unit that is configured to relatively move the mask with respect (Continued)

to the classification target image. The sum total brightness calculation unit is configured to calculate the sum total brightness of the each pixel within the classification target image every time the movement unit relatively moves the mask by a predetermined movement amount. The mask structure optimization device further includes a mask pattern optimization unit that is configured to optimize the mask pattern of the mask on the basis of the sum total brightness.

8 Claims, 20 Drawing Sheets

(51) Int. Cl.
*G01N 33/483* (2006.01)
*G06V 10/50* (2022.01)
*G06V 20/69* (2022.01)
*G06F 18/2115* (2023.01)
*G06F 18/21* (2023.01)
*G06N 3/045* (2023.01)

(52) U.S. Cl.
CPC ...... *G06F 18/2115* (2023.01); *G06F 18/2163* (2023.01); *G06N 3/045* (2023.01); *G06V 10/507* (2022.01); *G06V 20/695* (2022.01); *G06V 20/698* (2022.01)

(58) Field of Classification Search
CPC ............. G01N 33/4833; G06K 9/6231; G06K 9/6261; G06N 3/0454
See application file for complete search history.

(56) References Cited

U.S. PATENT DOCUMENTS

| | | |
|---|---|---|
| 2017/0213344 A1 | 7/2017 | Hong |
| 2017/0287137 A1 | 10/2017 | Lin |
| 2018/0246030 A1 | 8/2018 | Ota et al. |
| 2018/0374568 A1* | 12/2018 | Agnello ................ G16H 40/40 |
| 2019/0205606 A1* | 7/2019 | Zhou ................... G06N 3/0445 |

FOREIGN PATENT DOCUMENTS

| | | |
|---|---|---|
| WO | WO 2006/083969 A2 | 8/2006 |
| WO | WO 2016/136801 A1 | 9/2016 |
| WO | WO 2018/015414 A1 | 1/2018 |

OTHER PUBLICATIONS

Written Opinion dated Apr. 16, 2019 in corresponding PCT International Application No. PCT/JP2019/003120.

* cited by examiner

MASK STRUCTURE OPTIMIZATION DEVICE, MASK STRUCTURE OPTIMIZATION METHOD, AND PROGRAM

CROSS REFERENCE TO RELATED APPLICATIONS

The present application is a divisional under 37 C.F.R. § 1.53(b) of prior U.S. patent application Ser. No. 16/965,311, filed Jul. 28, 2020, which is a 35 U.S.C. § 371 National Phase conversion of PCT/JP2019/003120, filed Jan. 30, 2019, the contents of which are incorporated herein by reference, which claims priority of Japanese Patent Application No. 2018-014150, filed Jan. 30, 2018, the contents of which are incorporated by reference herein. The PCT International Application was published in the Japanese language.

TECHNICAL FIELD

The present invention relates to a mask structure optimization device, a mask structure optimization method, and a program.

BACKGROUND ART

In the related art, a method for performing analysis of cells or the like using an imaging flow cytometer is known (for example, refer to Patent Document 1). Patent Document 1 discloses the classification of images in accordance with cell types. Patent Document 1 further discloses use of a mask in the document. Incidentally, the mask disclosed in Patent Document 1 is realized by an operation in which a cell image detected by a time delay integration charge coupled device (TDI-CCD) is segmented through software. Meanwhile, a mask in the present invention is a physical mask, such as structured lighting or the like as disclosed, for example, in Patent Document 2, and it differs from the mask disclosed in Patent Document 1. The mask in the present invention is not used in Patent Document 1. In Patent Document 2, any one of or both optical systems having a structured lighting pattern or a structured detection system having a plurality of regions with different optical characteristics are used as a mask. Examples of a method for projecting a mask include a digital micro-mirror device (DMD), a spatial light modulator (SLM), an overhead projector (OHP), a light transmissive sheet, and a diffractive optical element (DOE).

Citation List—Patent Literature
Patent Document 1: Published Japanese Translation No. 2008-533440 of the PCT International Publication.
Patent Document 2: PCT International Publication No. WO2016/136801.

SUMMARY OF THE INVENTION

Technical Problem

In some technologies in the related art, there is concern that the classification accuracy of an image or the like of fine particles including cells or bacteria may not be able to be sufficiently improved.

In consideration of the foregoing problem, the present invention aims to provide a mask structure optimization device, a mask structure optimization method, and a program capable of sufficiently improving classification accuracy in a case in which fine particles or the like including cells are classified on the basis of morphological information.

Solution to Problem

According to an aspect of the present invention, there is provided a mask structure optimization device including a classification target image size acquisition unit that is configured to acquire a size of a classification target image which is an image including a classification target, a mask size setting unit that is configured to set a size of a mask applied to the classification target image, a brightness detection unit that is configured to detect a brightness of each pixel within the classification target image at a position on an opposite side of the mask from the classification target image, a sum total brightness calculation unit that is configured to calculate a sum total brightness of the each pixel within the classification target image detected by the brightness detection unit, an initial value setting unit that is configured to set an initial value for a mask pattern of the mask, and a movement unit that is configured to relatively move the mask with respect to the classification target image. The sum total brightness calculation unit is configured to calculate the sum total brightness of the each pixel within the classification target image every time the movement unit relatively moves the mask by a predetermined movement amount. The mask structure optimization device further includes a mask pattern optimization unit that is configured to optimize the mask pattern of the mask on the basis of the sum total brightness calculated by the sum total brightness calculation unit.

The mask structure optimization device according to the aspect of the present invention may further include an image addition unit that is configured to add a first dark image to one side of the classification target image and is configured to add a second dark image to the other side of the classification target image. The movement unit may relatively move the mask with respect to the classification target image in which the first dark image and the second dark image are added.

In the mask structure optimization device according to the aspect of the present invention, the size of the mask in a moving direction set by the mask size setting unit may be N pixels that is larger than a size of the classification target image in the moving direction. A size of the first dark image in the moving direction added to the one side of the classification target image by the image addition unit may be (N−1) pixels. A size of the second dark image in the moving direction added to the other side of the classification target image by the image addition unit may be (N−1) pixels.

In the mask structure optimization device according to the aspect of the present invention, the movement unit may relatively move the mask with respect to the image in which the first dark image and the second dark image are added from a state in which an end portion of the mask on the one side and an end portion of the first dark image on the one side coincide with each other to a state in which an end portion of the mask on the other side and an end portion of the second dark image on the other side coincide with each other.

In the mask structure optimization device according to the aspect of the present invention, the sum total brightness calculation unit may calculate the sum total brightness of the each pixel within the classification target image every time the movement unit relatively moves the mask by one pixel.

In the mask structure optimization device according to the aspect of the present invention, the initial value setting unit may set the initial value for the mask pattern of the mask on the basis of a Bernoulli distribution.

In the mask structure optimization device according to the aspect of the present invention, the mask pattern optimization unit may optimize the mask pattern of the mask using a binary convolutional neural network. Each convolutional weight of the binary convolutional neural network used by the mask pattern optimization unit may be either +1 or 0.

In the mask structure optimization device according to the aspect of the present invention, the mask pattern optimization unit may optimize the mask pattern of the mask using a binary convolutional neural network. Each convolutional weight of the binary convolutional neural network used by the mask pattern optimization unit may be either +1 or −1.

In the mask structure optimization device according to the aspect of the present invention, the mask of which the mask pattern is optimized by the mask structure optimization device may be used in an imaging flow cytometer.

In the mask structure optimization device according to the aspect of the present invention, the classification target may be a cell.

According to another aspect of the present invention, there is provided a mask structure optimization method including a classification target image size acquiring step of acquiring a size of a classification target image which is an image including a classification target, a mask size setting step of setting a size of a mask applied to the classification target image, a brightness detecting step of detecting a brightness of each pixel within the classification target image at a position on an opposite side of the mask from the classification target image, a sum total brightness calculating step of calculating a sum total brightness of the each pixel within the classification target image detected in the brightness detecting step, an initial value setting step of setting an initial value for a mask pattern of the mask, and a moving step of relatively moving the mask with respect to the classification target image. In the sum total brightness calculating step, the sum total brightness of the each pixel within the classification target image is calculated every time the mask is relatively moved by a predetermined movement amount. The mask structure optimization method further includes a mask pattern optimizing step of optimizing the mask pattern of the mask on the basis of the sum total brightness calculated in the sum total brightness calculating step.

According to another aspect of the present invention, there is provided a program for causing a computer to execute a classification target image size acquiring step of acquiring a size of a classification target image which is an image including a classification target, a mask size setting step of setting a size of a mask applied to the classification target image, a brightness detecting step of detecting a brightness of each pixel within the classification target image at a position on an opposite side of the mask from the classification target image, a sum total brightness calculating step of calculating a sum total brightness of the each pixel within the classification target image detected in the brightness detecting step, an initial value setting step of setting an initial value for a mask pattern of the mask, and a moving step of relatively moving the mask with respect to the classification target image. In the sum total brightness calculating step, the sum total brightness of the each pixel within the classification target image is calculated every time the mask is relatively moved by a predetermined movement amount. The program further causes the computer to execute a mask pattern optimizing step of optimizing the mask pattern of the mask on the basis of the sum total brightness calculated in the sum total brightness calculating step.

According to another aspect of the present invention, there is provided a mask structure optimization device including a classification target image size acquisition unit that is configured to acquire a size of a classification target image which is an image including a classification target, a mask size setting unit that is configured to set a size of a mask applied to the classification target image, an initial value setting unit that is configured to set an initial value for a mask pattern of the mask, a convolutional processing unit that is configured to execute convolutional processing for the classification target image and an image of the mask, and a mask pattern optimization unit that is configured to optimize the mask pattern of the mask on the basis of results of the convolutional processing executed by the convolutional processing unit.

The mask structure optimization device according to the aspect of the present invention may further include a classification target image processing unit that is configured to execute preprocessing for the classification target image. The classification target image processing unit may include a segmentation unit that is configured to execute processing of segmenting a plurality of classification target images from an original image including a plurality of classification targets. At least one classification target may be included in each classification target image segmented by the segmentation unit. The classification target image processing unit may further include an exclusion unit that is configured to exclude a classification target image in which at least one classification target is positioned on an image outer edge portion from the plurality of classification target images segmented by the segmentation unit.

In the mask structure optimization device according to the aspect of the present invention, the classification target image processing unit may further include a perturbation unit that is configured to execute perturbation processing for each classification target image after processing is executed by the exclusion unit. The perturbation unit may generate a post-perturbation classification target image that is a classification target image in which a position of the one classification target included in each classification target image is moved from each classification target image after processing is executed by the exclusion unit without moving a position of the image outer edge portion of each classification target image.

In the mask structure optimization device according to the aspect of the present invention, the classification target image and the mask may have a rectangular shape. A dimension of a short side of the mask may be smaller than a dimension of a long side of the classification target image and a dimension of a short side of the classification target image.

According to another aspect of the present invention, there is provided a mask structure optimization method including a classification target image size acquiring step of acquiring a size of a classification target image which is an image including a classification target, a mask size setting step of setting a size of a mask applied to the classification target image, an initial value setting step of setting an initial value for a mask pattern of the mask, a convolutional processing step of executing convolutional processing for the classification target image and an image of the mask, and a mask pattern optimizing step of optimizing the mask pattern of the mask on the basis of results of the convolutional processing executed in the convolutional processing step.

According to another aspect of the present invention, there is provided a program for causing a computer to execute a classification target image size acquiring step of acquiring a size of a classification target image which is an image including a classification target, a mask size setting step of setting a size of a mask applied to the classification target image, an initial value setting step of setting an initial value for a mask pattern of the mask, a convolutional processing step of executing convolutional processing for the classification target image and an image of the mask, and a mask pattern optimizing step of optimizing the mask pattern of the mask on the basis of results of the convolutional processing executed in the convolutional processing step.

Advantageous Effects of Invention

According to the present invention, it is possible to provide a mask structure optimization device, a mask structure optimization method, and a program which enable sufficient improvement of classification accuracy in a case in which fine particles or the like including cells are classified on the basis of morphological information.

BRIEF DESCRIPTION OF DRAWINGS

FIG. 2 is a drawing showing a classification target image, a mask, and the like.

DESCRIPTION OF EMBODIMENTS

Hereinafter, with reference to the drawings, embodiments of a mask structure optimization device, a mask structure optimization method, and a program according to the present invention are described.

First Embodiment

Figure 1:
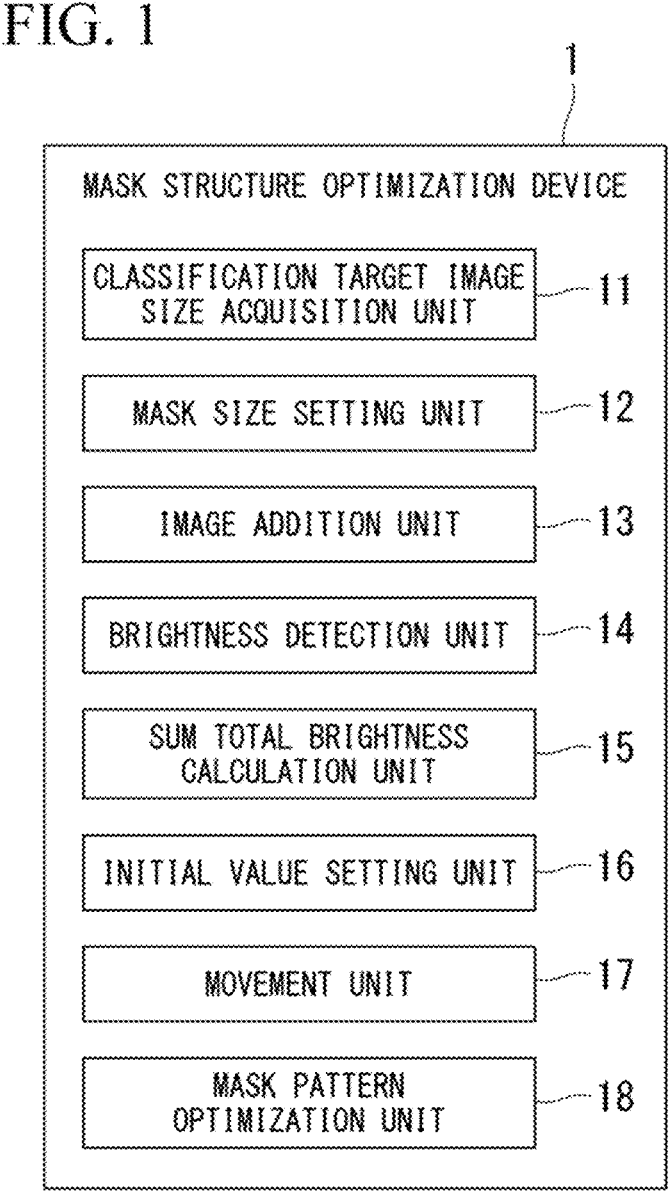
FIG. 1 is a drawing showing an example of a configuration of a mask structure optimization device of a first embodiment.

FIG. 1 is a drawing showing an example of a configuration of a mask structure optimization device 1 of a first embodiment.

In the example shown in FIG. 1, a mask structure optimization device 1 includes a classification target image size acquisition unit 11, a mask size setting unit 12, an image addition unit 13, a brightness detection unit 14, a sum total brightness calculation unit 15, an initial value setting unit 16, a movement unit 17, and a mask pattern optimization unit 18.

The classification target image size acquisition unit 11 acquires a size of a classification target image which is an image including a classification target. Examples of "a classification target" include a cell, a bacterium, or a spheroidal cell aggregate. "A classification target image" is a two-dimensional image including a classification target. The classification target image size acquisition unit 11 acquires the size (longitudinal dimension×crosswise dimension) of a classification target image.

The mask size setting unit 12 sets the size (longitudinal dimension×crosswise dimension) of a mask applied to a classification target image.

In the example shown in FIG. 1, a mask applied to a classification target image is a mask having light transmitting portions and light shielding portions, such as a binary mask, for example. In another example, a mask applied to a classification target image may be a mask other than a binary mask, such as a halftone mask, for example.

In the example shown in FIG. 1, the image addition unit 13 adds a first image to the left side of the classification target image and adds a second image to the right side of the classification target image.

In the example shown in FIG. 1, the image addition unit 13 adds a dark image as the first image to the left side of the classification target image. However, in another example, as the first image, for example, the image addition unit 13 may add an image in another color having a brightness of the same degree as that of a dark image (specifically, an image in a color which does not contribute to increase of the sum total brightness calculated by the sum total brightness calculation unit 15) to the left side of a classification target image.

Similarly, in the example shown in FIG. 1, the image addition unit 13 adds a dark image as the second image to the right side of the classification target image. However, in another example, as the second image, for example, the image addition unit 13 may add an image in another color having a brightness of the same degree as that of a dark image to the right side of a classification target image. Alternatively, in another example, the image addition unit 13 may perform irradiation with a structured lighting pattern.

In the example shown in FIG. 1, the brightness detection unit 14 detects the brightness of each pixel within the classification target image at a position on an opposite side of the mask from the classification target image. That is, the brightness detection unit 14 detects light from the classification target image transmitted through the light transmitting portions of the mask.

The sum total brightness calculation unit 15 calculates the sum total brightness of the each pixel within the classification target image detected by the brightness detection unit 14. When the proportion of light transmitting portions of a mask positioned between the brightness detection unit 14 and a classification target image increases, that is, when a light transmittance of a mask increases, the sum total brightness calculated by the sum total brightness calculation unit 15 increases.

In the example shown in FIG. 1, as described above, the brightness detection unit 14 detects light from the classification target image transmitted through the light transmitting portions of the mask and does not detect light from the classification target image which has not been transmitted through the light transmitting portions of the mask. For this reason, when no mask is positioned between the brightness detection unit 14 and a classification target image, there is no light from the classification target image transmitted through the light transmitting portions of the mask, and thus no light is detected by the brightness detection unit 14. As a result, when no mask is positioned between the brightness detection unit 14 and a classification target image, the sum total brightness calculated by the sum total brightness calculation unit 15 becomes zero.

The initial value setting unit 16 sets an initial value for a mask pattern of a mask. "A mask pattern" denotes a disposition configuration of the light transmitting portions and the light shielding portions in a mask. Specifically, when a mask pattern of a first mask and a mask pattern of a second mask are identical to each other, positions where the light transmitting portions are disposed are the same between the first mask and the second mask, and positions where the light shielding portions are disposed are the same between the first mask and the second mask.

That is, the initial value setting unit 16 determines an initial (first) mask pattern of a mask. As described below, the mask pattern of a mask is changed by the mask pattern optimization unit 18 as necessary.

In the example shown in FIG. 1, the initial value setting unit 16 sets the initial value for the mask pattern of the mask on the basis of a Bernoulli distribution. That is, the initial value setting unit 16 determines the initial mask pattern of the mask on the basis of a Bernoulli distribution.

In another example, the initial value setting unit 16 may set the initial value for the mask pattern of a mask by an arbitrary technique not using a Bernoulli distribution.

In the example shown in FIG. 1, the movement unit 17 relatively moves the mask with respect to the classification target image.

In the example shown in FIG. 2 (which is described below), the movement unit 17 moves a classification target image with respect to a fixed mask. However, in another example, the movement unit 17 may move a mask with respect to a fixed classification target image.

In the example shown in FIG. 1, every time the movement unit 17 relatively moves the mask with respect to the classification target image by a predetermined movement amount, the brightness detection unit 14 detects the brightness of the each pixel within the classification target image, and the sum total brightness calculation unit 15 calculates the sum total brightness of the each pixel within the classification target image.

The mask pattern optimization unit 18 optimizes the mask pattern of the mask (changes the mask pattern) on the basis of the sum total brightness calculated by the sum total brightness calculation unit 15.

In an analyzer (not shown) performing analysis and classification of a classification target, for example, a mask having a mask pattern optimized by the mask pattern optimization unit 18 is used. Consequently, the classification accuracy can be improved compared to when no mask is used or when a mask having a mask pattern set on the basis of a Bernoulli distribution or the like (that is, a mask having a mask pattern which is not optimized) is used, for example.

Figure 2:
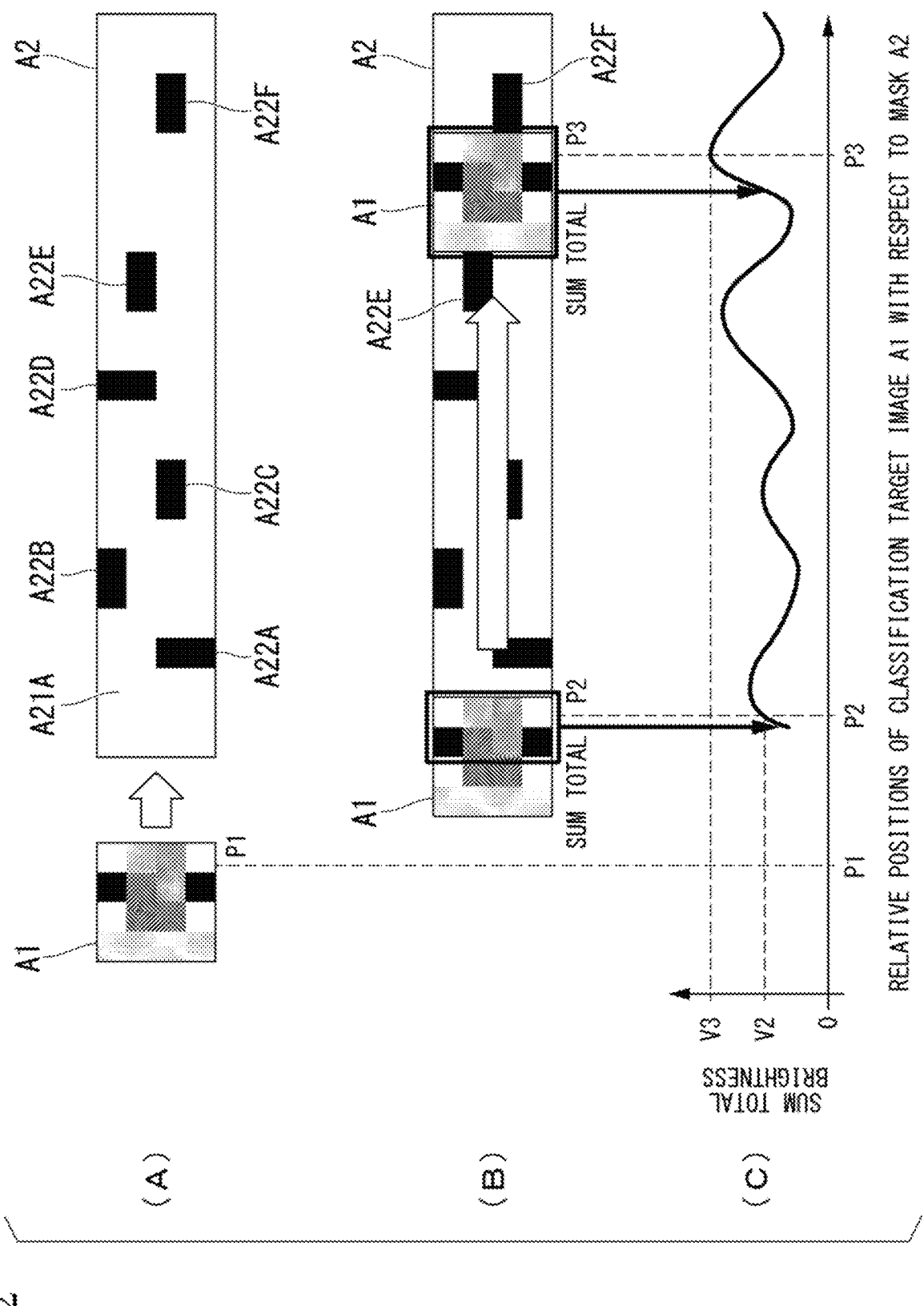

FIG. 2 is a drawing showing a classification target image A1, a mask A2, and the like. Specifically, (A) of FIG. 2 is a drawing showing a relationship between the classification target image A1 positioned at a position P1 and the mask A2. (B) of FIG. 2 is a drawing showing a relationship between the classification target image A1 positioned at a position P2 and the mask A2 and a relationship between the classification target image A1 positioned at a position P3 and the mask A2. (C) of FIG. 2 is a drawing showing a relationship between relative positions of the classification target image A1 with respect to the mask A2 and the sum total brightness. The horizontal axis in (C) of FIG. 2 indicates the relative positions of the classification target image A1 with respect to the mask A2. The vertical axis in (C) of FIG. 2 indicates the sum total brightness at each relative position of the classification target image A1 with respect to the mask A2.

In the example shown in FIG. 2, as indicated by arrows in (A) and (B) of FIG. 2, the classification target image A1 is moved by the movement unit 17 to the right from the position P1 on the left side of the mask A2. The mask A2 includes a light transmitting portion A21A and light shielding portions A22A, A22B, A22C, A22D, A22E, and A22F.

When the classification target image A1 is positioned at the position P1, the mask A2 is not positioned between the brightness detection unit 14 and the classification target image A1. Therefore, there is no light from the classification target image A1 transmitted through the light transmitting portion A21A of the mask A2. As a result, as shown in (C) of FIG. 2, the sum total brightness calculated by the sum total brightness calculation unit 15 becomes zero.

When the classification target image A1 is positioned at the position P2, light from the right half part of the classification target image A1 is transmitted through the light transmitting portion A21A of the mask A2, but light from the left half part of the classification target image A1 is not transmitted through the light transmitting portion A21A of the mask A2. As a result, as shown in (C) of FIG. 2, the sum total brightness calculated by the sum total brightness calculation unit 15 becomes a value V2 which is comparatively small.

When the classification target image A1 is positioned at the position P3, light from the entire classification target image A1 is transmitted through the light transmitting portion A21A of the mask A2. In addition, neither the light shielding portion A22E nor A22F of the mask A2 is positioned between the brightness detection unit 14 and the classification target image A1. As a result, as shown in (C)

of FIG. 2, the sum total brightness calculated by the sum total brightness calculation unit 15 becomes a maximum value V3.

In a process in which the mask A2 moves from the position P2 to the position P3, the light shielding portions A22A, A22B, A22C, A22D, and A22E of the mask A2 are positioned in order between the brightness detection unit 14 and the classification target image A1. As a result, as shown in (C) of FIG. 2, the sum total brightness calculated by the sum total brightness calculation unit 15 increases or decreases.

Figure 3:
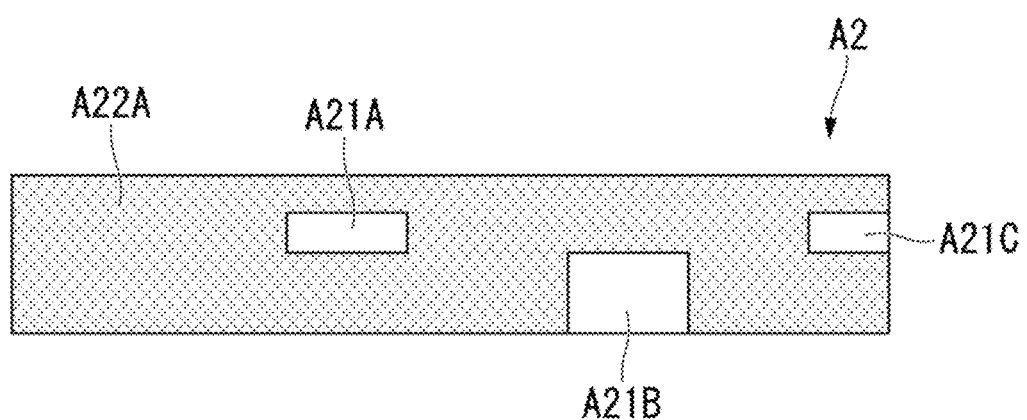
FIG. 3 is a drawing showing another example of the mask.

FIG. 3 is a drawing showing another example of the mask A2.

In the example shown in FIG. 3, the mask A2 includes light transmitting portions A21A, A21B, and A21C and the light shielding portion A22A.

A light transmittance p of the mask A2 is 90% in the example shown in (A) and (B) of FIG. 2, whereas the light transmittance p of the mask A2 is 10% in the example shown in FIG. 3.

Figure 4:
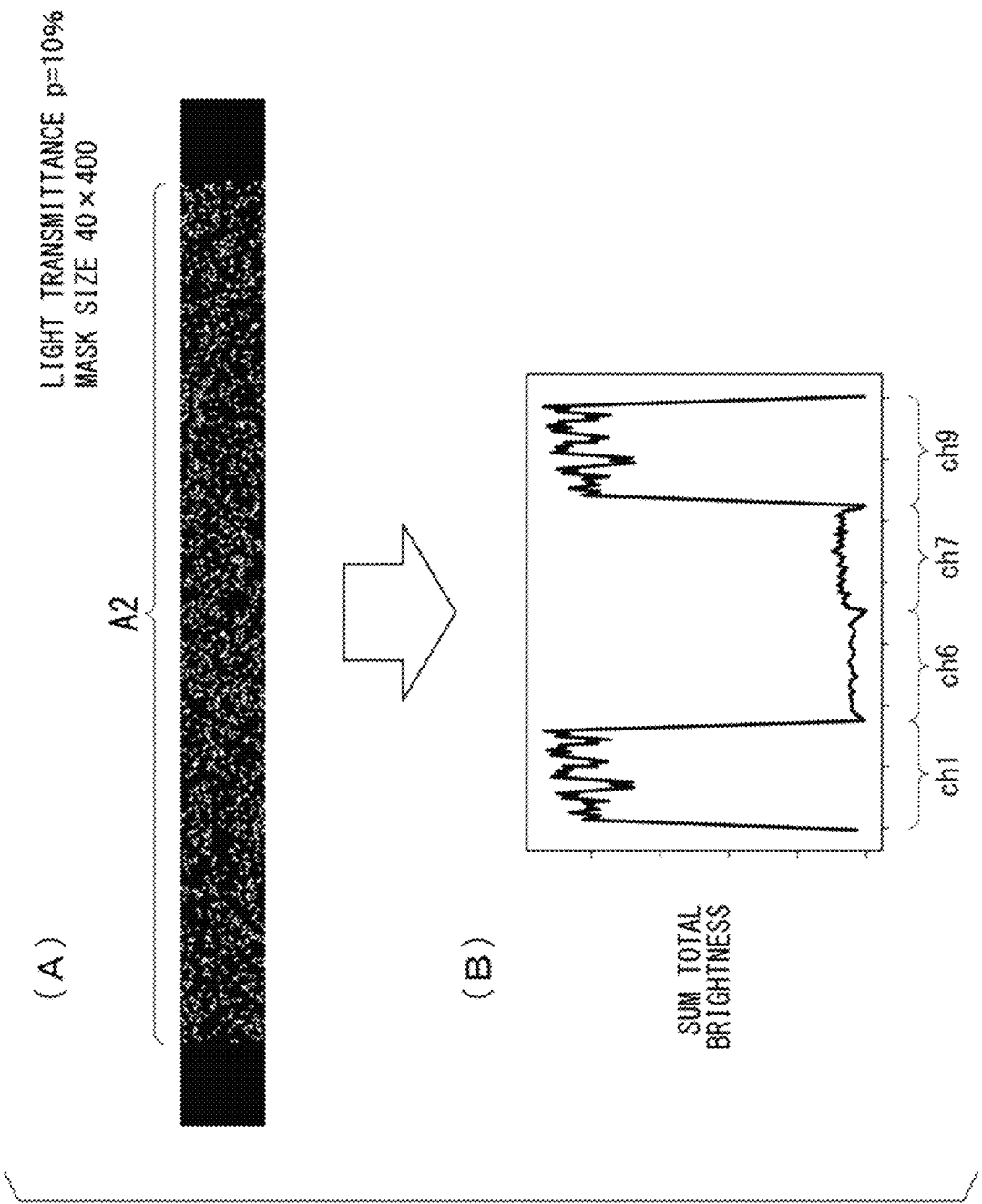
FIG. 4 is a drawing showing another example or the like of the mask.

FIG. 4 is a drawing showing another example or the like of the mask A2. Specifically, (A) of FIG. 4 shows another example of the mask A2. (B) of FIG. 4 shows a waveform of the sum total brightness obtained when the mask A2 shown in (A) of FIG. 4 is relatively moved with respect to the classification target image.

In the example shown in FIG. 4, the mask A2 has a mask size of 40 pixels in height×400 pixels in width. In addition, the light transmittance p of the mask A2 is 10%. The classification target image relatively moved with respect to the mask A2 has a classification target image size of 40 pixels in height×40 pixels in width.

In (B) of FIG. 4, the section "ch1" indicates a waveform of the sum total brightness obtained under a first condition when the mask A2 is relatively moved with respect to the classification target image from a first state in which the right end of the classification target image and the left end of the mask A2 coincide with each other to a second state in which the left end of the classification target image and the right end of the mask A2 coincide with each other. The first condition indicates a case in which the sum total of R values of an RGB color system is used as the sum total brightness, for example.

The section "ch6" indicates a waveform of the sum total brightness obtained under a second condition when the mask A2 is relatively moved with respect to the classification target image from the first state to the second state. The second condition indicates a case in which the sum total of G values of the RGB colorimetric system is used as the sum total brightness, for example.

The section "ch7" indicates a waveform of the sum total brightness obtained under a third condition when the mask A2 is relatively moved with respect to the classification target image from the first state to the second state. The third condition indicates a case in which the sum total of B values of the RGB colorimetric system is used as the sum total brightness, for example.

The section "ch9" indicates a waveform of the sum total brightness obtained under a fourth condition differing from the first to third conditions when the mask A2 is relatively moved with respect to the classification target image from the first state to the second state.

Figure 5:
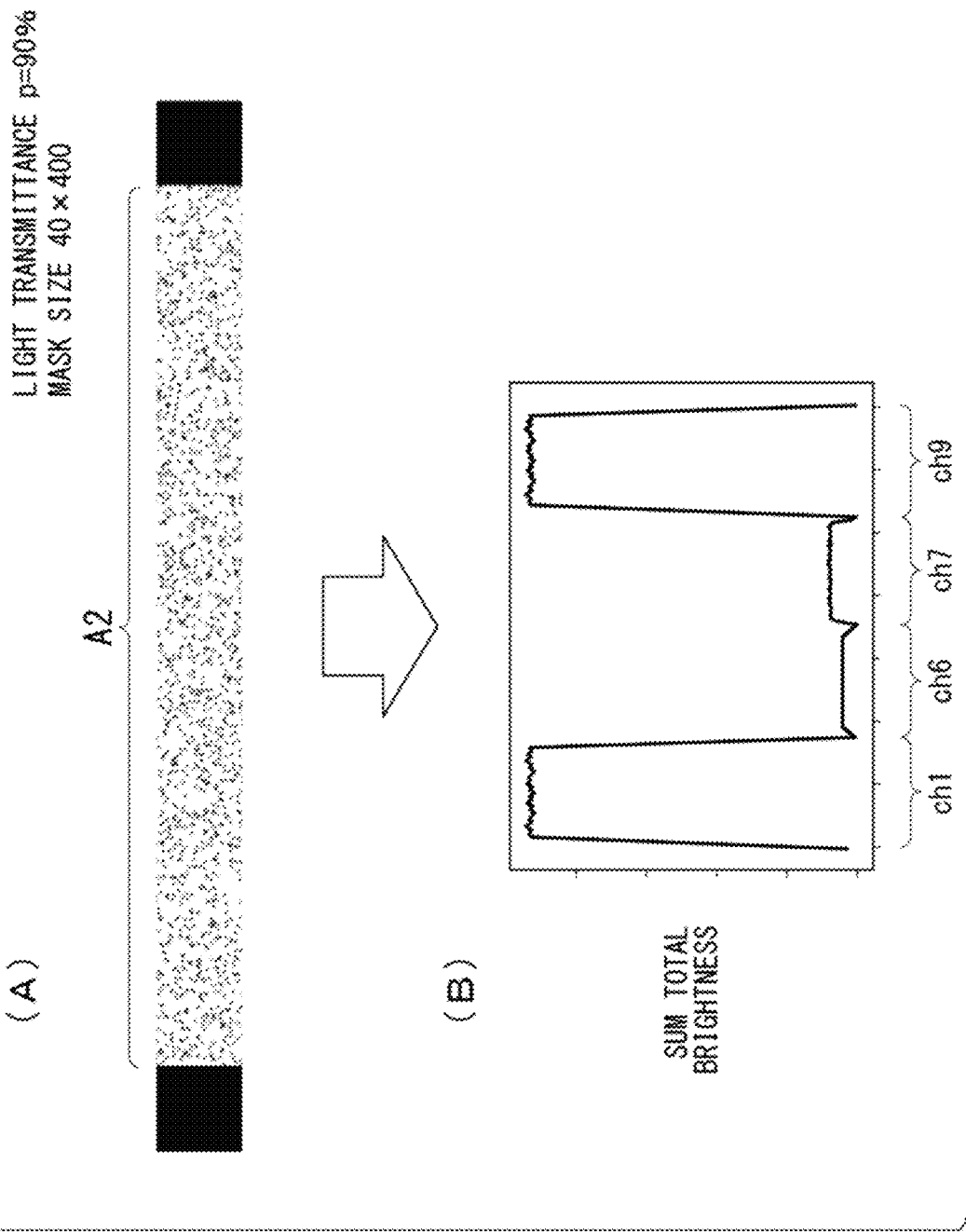
FIG. 5 is another drawing showing another example or the like of the mask.

FIG. 5 is a drawing showing another example or the like of the mask A2. Specifically, (A) of FIG. 5 shows another example of the mask A2. (B) of FIG. 5 shows a waveform of the sum total brightness obtained when the mask A2 shown in (A) of FIG. 5 is relatively moved with respect to the classification target image.

In the example shown in FIG. 5, the mask A2 has a mask size of 40 pixels in height×400 pixels in width. In addition, the light transmittance p of the mask A2 is 90%. The classification target image relatively moved with respect to the mask A2 has a classification target image size of 40 pixels in height×40 pixels in width.

In (B) of FIG. 5, the section "ch1" indicates a waveform of the sum total brightness obtained under the first condition described above when the mask A2 is relatively moved with respect to the classification target image from the first state described above to the second state described above.

The section "ch6" indicates a waveform of the sum total brightness obtained under the second condition described above when the mask A2 is relatively moved with respect to the classification target image from the first state to the second state.

The section "ch7" indicates a waveform of the sum total brightness obtained under the third condition described above when the mask A2 is relatively moved with respect to the classification target image from the first state to the second state.

The section "ch9" indicates a waveform of the sum total brightness obtained under the fourth condition described above when the mask A2 is relatively moved with respect to the classification target image from the first state to the second state.

Figure 6:
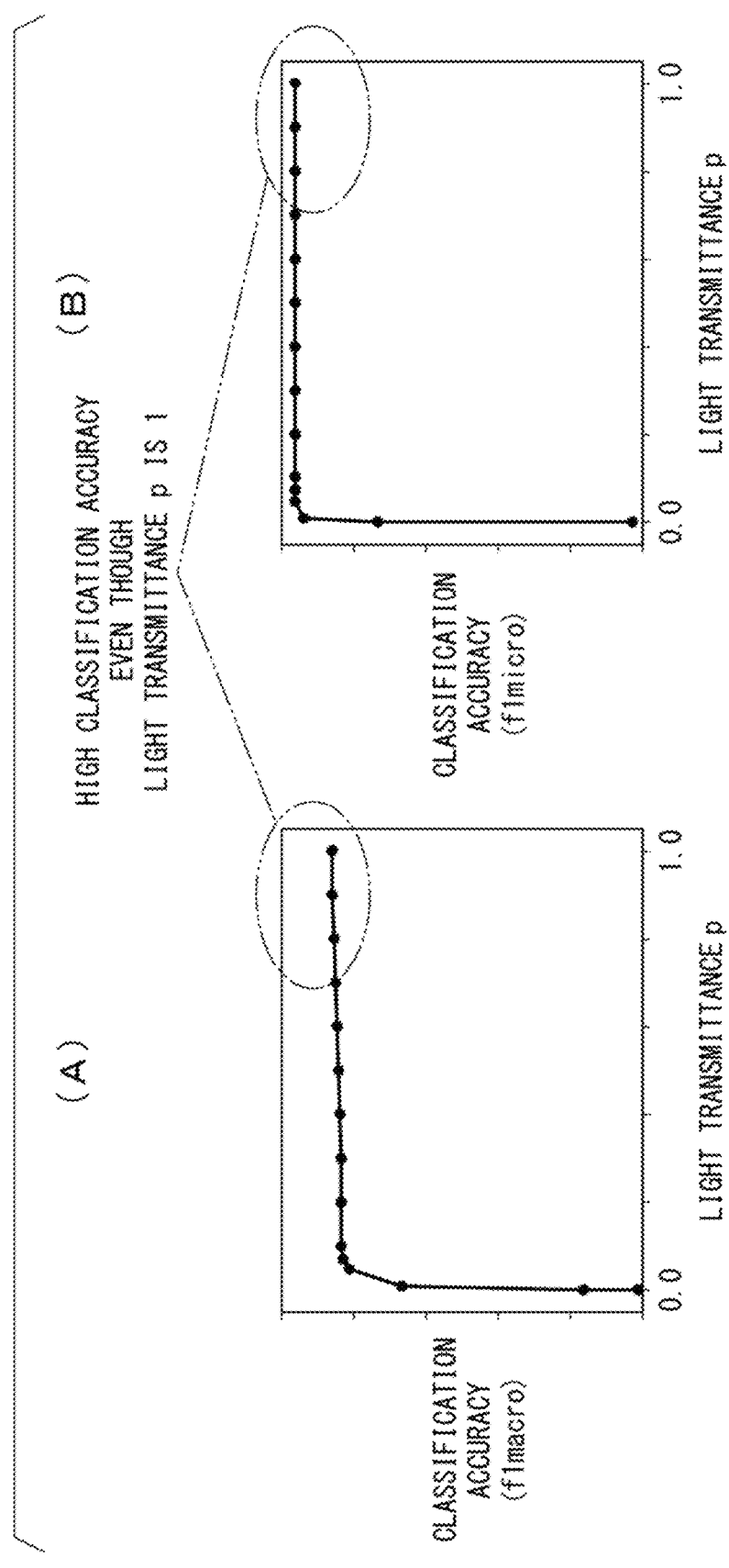
FIG. 6 is a drawing showing a relationship between a light transmittance of a mask and classification accuracy.

FIG. 6 is a drawing showing a relationship between the light transmittance p of the mask A2 and classification accuracy.

Specifically, in the example shown in (A) of FIG. 6, known "f1 macro" is used as an accuracy index. In the example shown in (B) of FIG. 6, known "f1 micro" is used as an accuracy index. The horizontal axes in (A) and (B) of FIG. 6 indicate the light transmittance p of the mask A2. The vertical axis in (A) of FIG. 6 indicates the classification accuracy of a predetermined classification target when the mask A2 having the light transmittance p is used and when the accuracy index "f1 macro" is used. The vertical axis in (B) of FIG. 6 indicates the classification accuracy of the classification target when the mask A2 having the light transmittance p is used and when the accuracy index "f1 micro" is used.

According to the examples shown in (A) and (B) of FIG. 6, when the light transmittance p increases, the classification accuracy of the classification target becomes higher. That is, at first glance, it seems that the classification accuracy of the classification target is higher when the mask A2 is not positioned between the brightness detection unit 14 and the classification target image A1.

However, as described below, the inventors have found through intensive research that the classification accuracy deteriorates depending on the classification target when the light transmittance p becomes 1 (100%).

On the other hand, it has been found that the classification accuracy can be improved considerably with only the information such as "the sum total brightness of each pixel within a classification target image". Specifically, in the example shown in FIG. 4, the sum total brightness of "ch1", the sum total brightness of "ch6", the sum total brightness of "ch7", and the sum total brightness of "ch9" are taken as the feature of the classification target of the example shown in FIG. 4. As a result, the classification target of the example shown in FIG. 4 can be classified with high accuracy.

Figure 7:
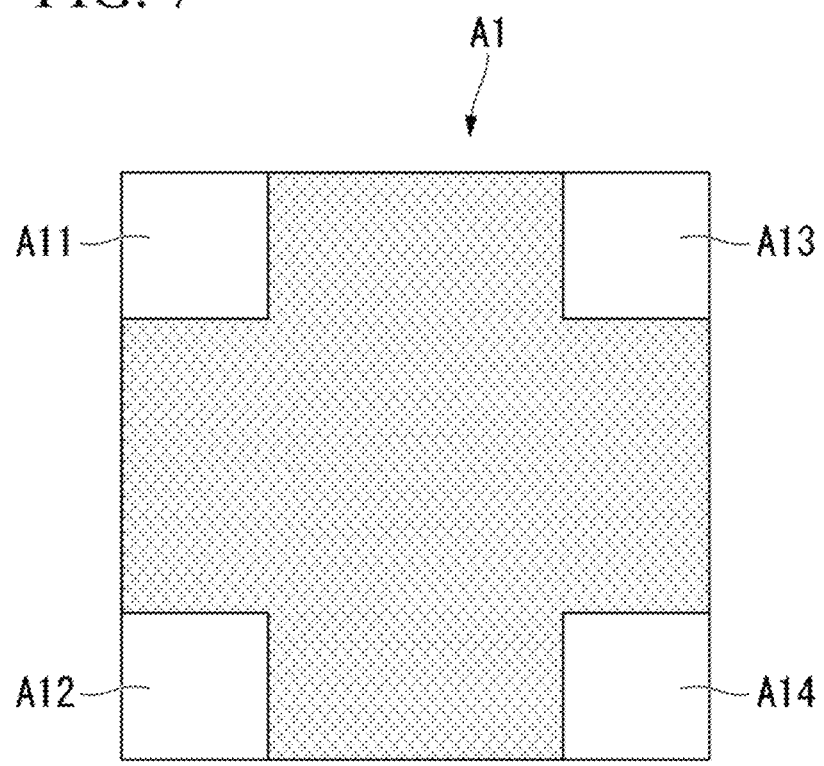
FIG. 7 is a drawing showing corner portions of a classification target image.

FIG. 7 is a drawing showing corner portions A11, A12, A13, and A14 of the classification target image A1. Specifically, FIG. 7 is a drawing showing a part of verification performed in research of the inventors.

In the example shown in FIG. 7, the sum total brightness of each pixel in the entire classification target image A1 is not used as the feature amount of the classification target, but the sum total brightness of each pixel in the corner portions A11, A12, A13, and A14 of the classification target image A1 is used as the feature amount of the classification target.

In the example shown in FIG. 7, the classification target image A1 has a size of 40 pixels in height×40 pixels in width. The corner portions A11, A12, A13, and A14 have a square shape and have a size of n pixels in height×n pixels in width. The classification accuracy of the classification target was verified by setting the value of n to 4, 8, 12, 16, and 20. When the value of n decreases, the classification accuracy of the classification target becomes lower.

Figure 8:
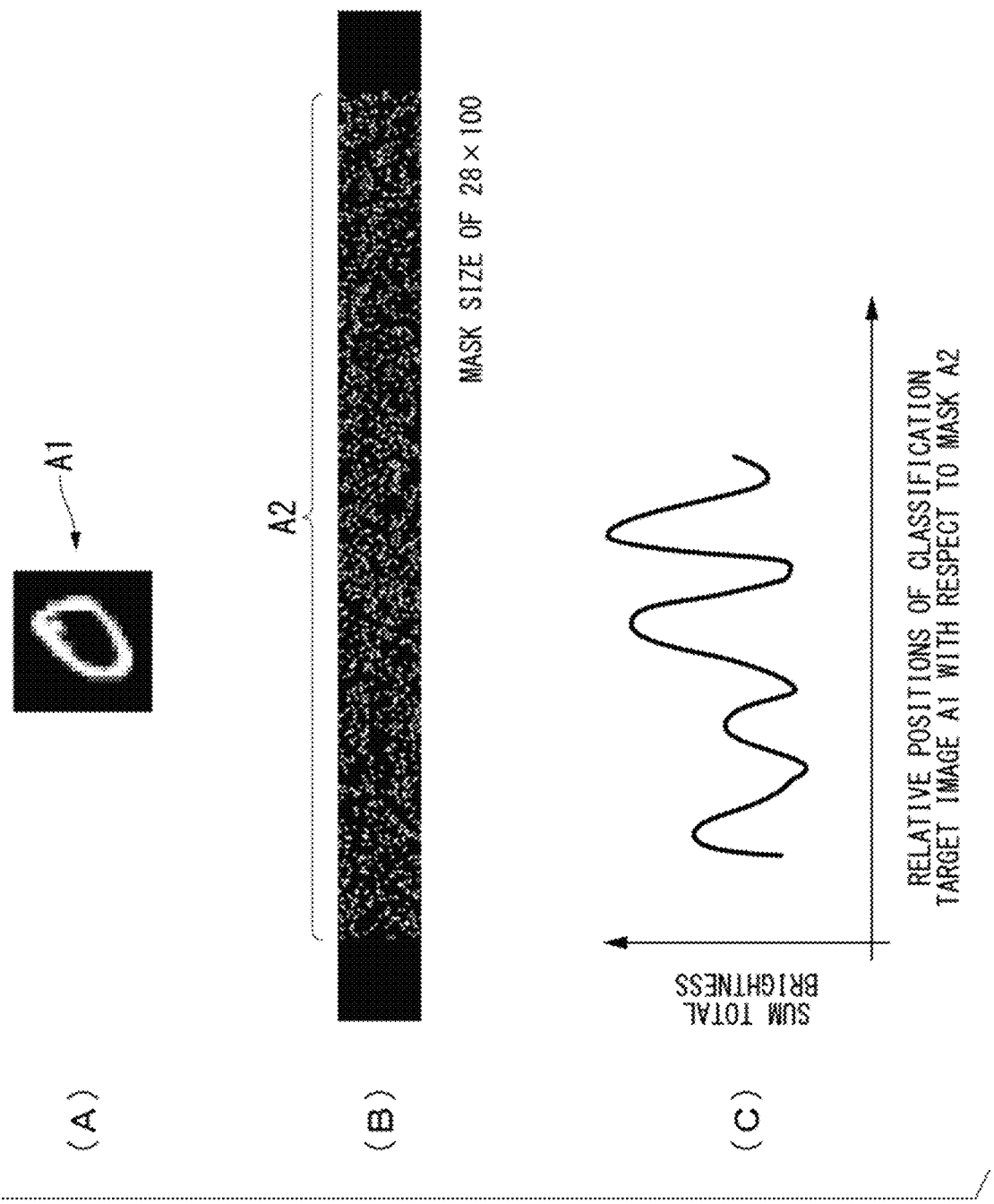
FIG. 8 is a drawing showing an example in which data of an MNIST is used as a classification target.

FIG. 8 is a drawing showing an example in which data of a Mixed National Institute of Standards and Technology database (MNIST) is used as a classification target. Specifically, (A) of FIG. 8 shows the classification target image A1 of a handwritten character "0". (B) of FIG. 8 shows the mask A2 applied to the classification target image A1 shown in (A) of FIG. 8. (C) of FIG. 8 is a drawing showing a relationship between relative positions of the classification target image A1 with respect to the mask A2 and the sum total brightness. The horizontal axis in (C) of FIG. 8 indicates the relative positions of the classification target image A1 with respect to the mask A2. The vertical axis in (C) of FIG. 8 indicates the sum total brightness at each relative position of the classification target image A1 with respect to the mask A2.

Specifically, (C) of FIG. 8 shows a waveform of the sum total brightness obtained when the classification target image A1 is relatively moved with respect to the mask A2 from a state in which the right end of the classification target image A1 and the left end of the mask A2 coincide with each other to a state in which the left end of the classification target image A1 and the right end of the mask A2 coincide with each other.

In the example shown in FIG. 8, the classification target image A1 has a classification target image size of 28 pixels in height×28 pixels in width. The mask A2 has a mask size of 28 pixels in height×100 pixels in width. The light transmittance p of the mask A2 is 10%. The mask pattern of the mask A2 is set on the basis of a Bernoulli distribution.

Figure 9:
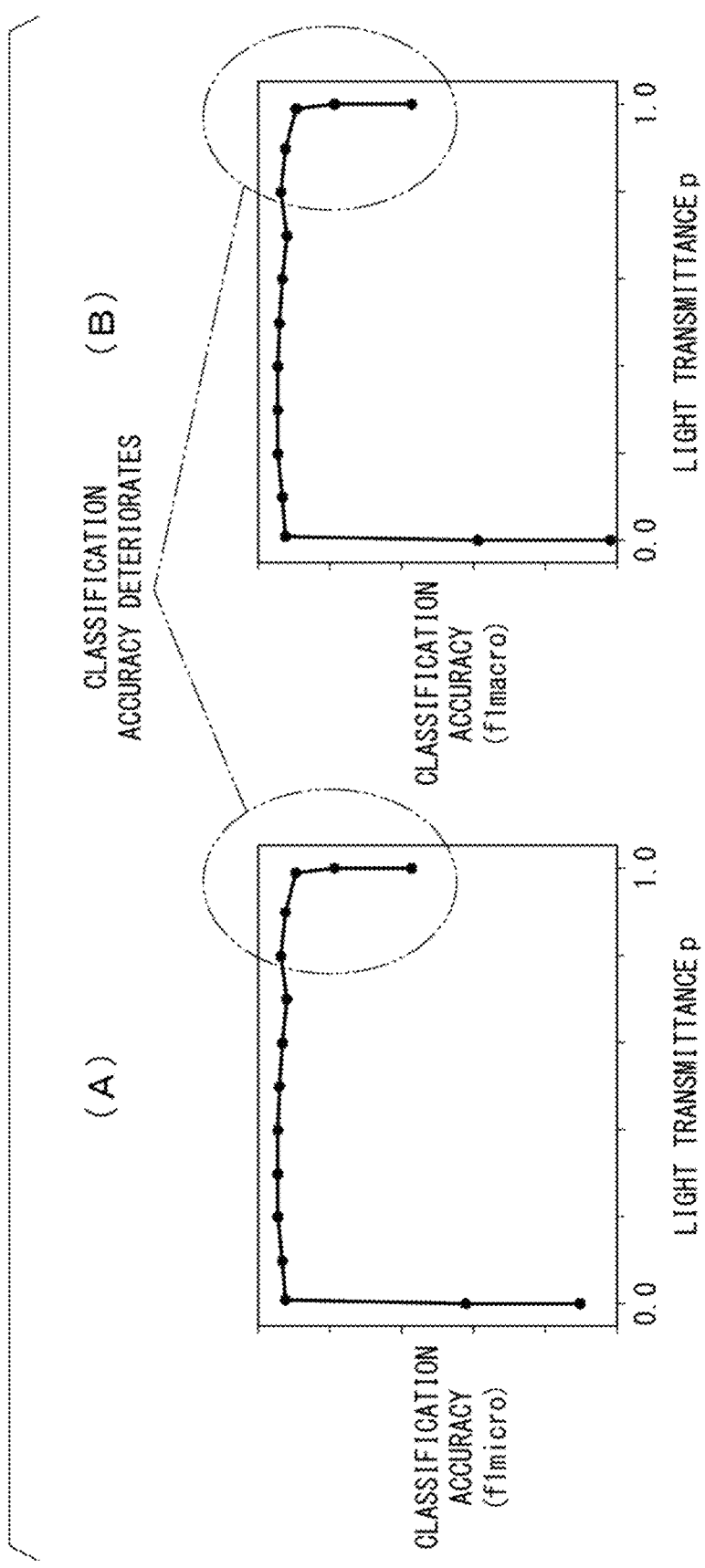
FIG. 9 is a drawing showing a relationship between the light transmittance of a mask and the classification accuracy of the classification target image shown in (A) of FIG. 8.

FIG. 9 is a drawing showing a relationship between the light transmittance p of the mask A2 and the classification accuracy of the classification target image A1 shown in (A) of FIG. 8.

Specifically, in the example shown in (A) of FIG. 9, the classification target image A1 of the handwritten character "0" shown in (A) of FIG. 8 is used, and the accuracy index "f1 micro" is used. In the example shown in (B) of FIG. 9, the classification target image A1 of the handwritten character "0" shown in (A) of FIG. 8 is used, and the accuracy index "f1 macro" is used. The horizontal axes in (A) and (B) of FIG. 9 indicate the light transmittance p of the mask A2. The vertical axis in (A) of FIG. 9 indicates the classification accuracy of the classification target image A1 of the handwritten character "0" when the mask A2 having the light transmittance p is used and when the accuracy index "f1 micro" is used. The vertical axis in (B) of FIG. 9 indicates the classification accuracy of the classification target image A1 of the handwritten character "0" when the mask A2 having the light transmittance p is used and when the accuracy index "f1 macro" is used.

The inventors have found through their research that as shown in (A) and (B) of FIG. 9, when the classification target image A1 is the handwritten character "0" shown in (A) of FIG. 8, differing from when the classification target image A1 is a cell image, the classification accuracy of the classification target image A1 deteriorates if the mask A2 having the light transmittance p of 100% is used.

If the mask A2 having the light transmittance p of 100% is used, for example, an integral value (of the waveform) of the sum total brightness as shown in (C) of FIG. 8 becomes substantially equivalent to each other in both a case in which the classification target image A1 is a handwritten character "6" and a case in which the classification target image A1 is a handwritten character "9". For this reason, the classification accuracy cannot be sufficiently improved by only using the mask A2 having the light transmittance p of 100% and analyzing the waveform of the sum total brightness as shown in (C) of FIG. 8.

Here, the inventors have attempted to sufficiently improve the classification accuracy using the mask A2 having the light transmittance p smaller than 100%.

Figure 10:
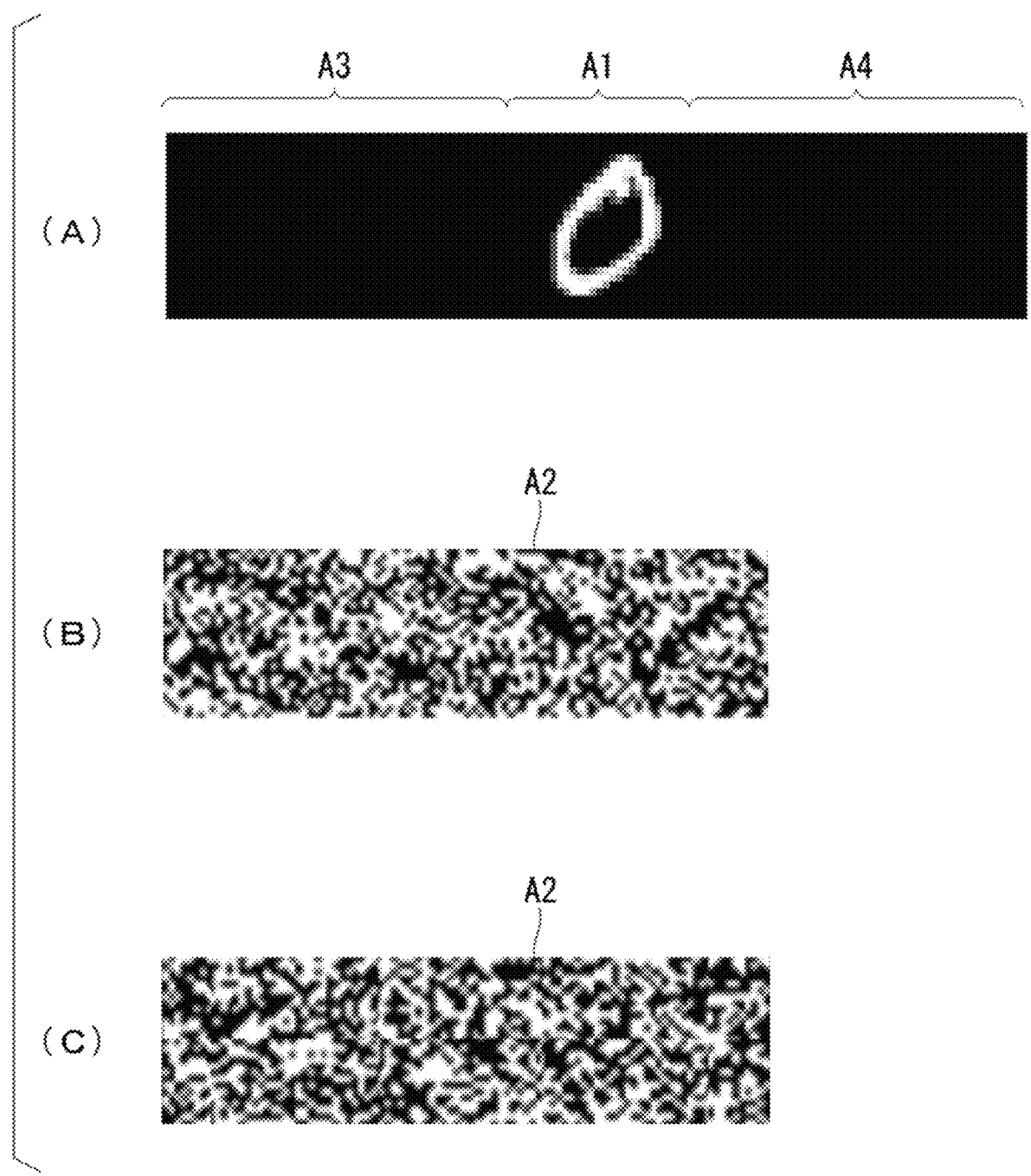
FIG. 10 is a drawing showing features of the present invention.
Figure 11:
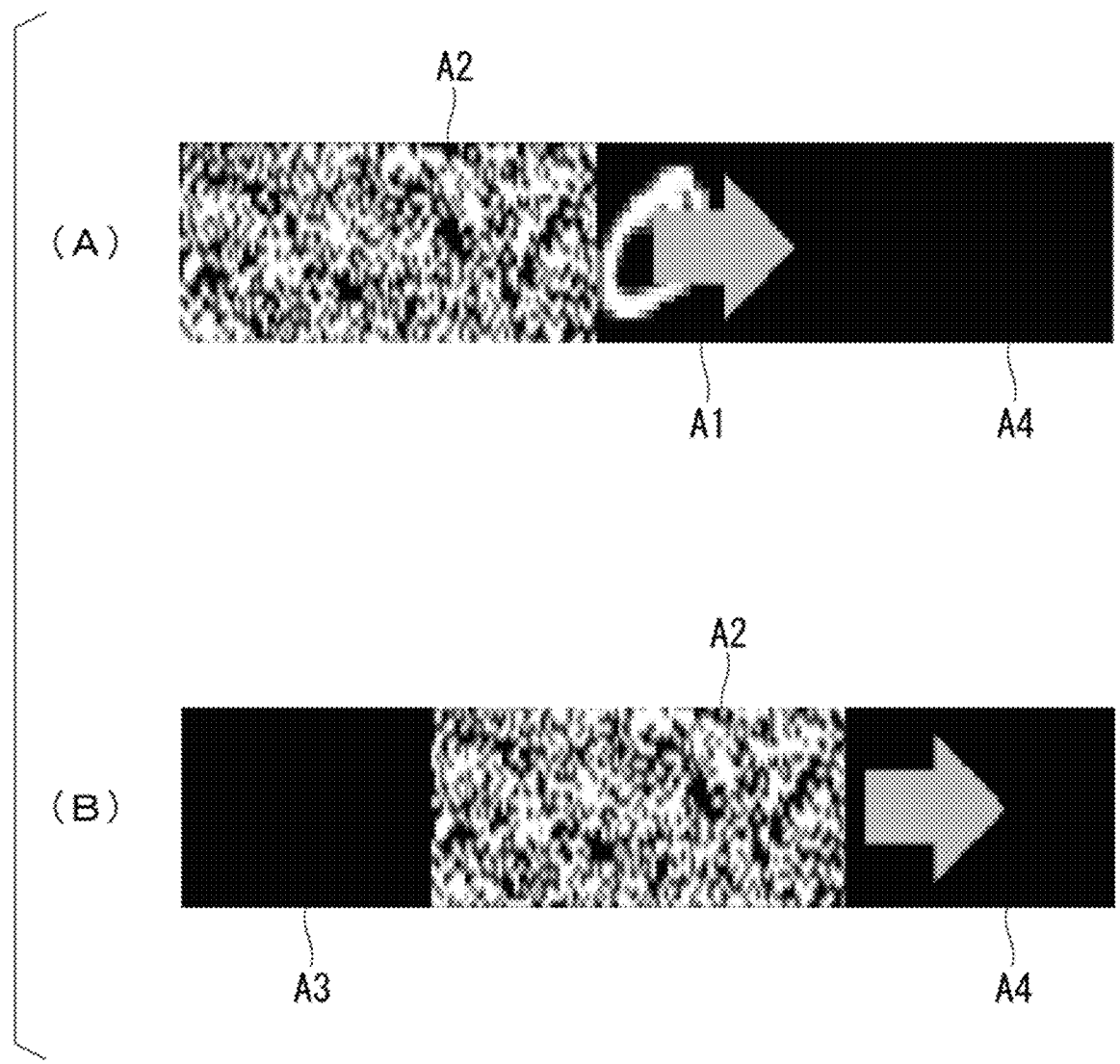
FIG. 11 is another drawing showing features of the present invention.

FIGS. 10 and 11 are drawings showing features of the present invention.

Specifically, (A) of FIG. 10 is a drawing showing a first image A3 and a second image A4 added to the classification target image A1 by the image addition unit 13. (B) of FIG. 10 is a drawing showing the mask A2 in which the initial value for the mask pattern is set by the initial value setting unit 16. (C) of FIG. 10 is a drawing showing the mask A2 having a mask pattern optimized by the mask pattern optimization unit 18.

(A) of FIG. 11 is a drawing showing a state when the mask A2 starts to be relatively moved with respect to the classification target image A1, the first image A3, and the second image A4. (B) of FIG. 11 is a drawing showing a halfway state while the mask A2 is relatively moved with respect to the classification target image A1, the first image A3, and the second image A4.

In the examples shown in FIGS. 10 and 11, the classification target image A1 has a classification target image size of 28 pixels in height×28 pixels in width. The mask A2 has a mask size of 28 pixels in height×100 pixels in width. The light transmittance p of the mask A2 is smaller than 1.

As shown in (A) of FIG. 10, the first image A3 is added to the left side of the classification target image A1 by the image addition unit 13. The second image A4 is added to the right side of the classification target image A1 by the image addition unit 13. In the examples shown in FIGS. 10 and 11, the first image A3 and the second image A4 are dark images.

In the examples shown in FIGS. 10 and 11, the mask A2 (refer to (B) of FIG. 10) in which the initial value for the mask pattern is set by the initial value setting unit 16 is generated.

The movement unit 17 relatively moves the mask A2 shown in (B) of FIG. 10 to the right in FIGS. 10 and 11 with respect to the classification target image A1, the first image A3, and the second image A4.

Specifically, the movement unit 17 relatively moves the mask A2 shown in (B) of FIG. 10 to the right in FIGS. 10 and 11 with respect to the classification target image A1, the first image A3, and the second image A4 from a state in which a left end portion of the mask A2 and a left end portion of the first image A3 coincide with each other (state shown in (A) of FIG. 11) to a state in which a right end portion of the mask A2 and a right end portion of the second image A4 coincide with each other.

Specifically, in the examples shown in FIGS. 10 and 11, the brightness detection unit 14 detects the brightness of pixels of a part (28 pixels in height×1 pixel in width) of the classification target image A1 overlapping with the mask A2 in a state in which a left end portion of the classification target image A1 and the right end portion of the mask A2 overlaps each other by one pixel (state shown in (A) of FIG. 11). The sum total brightness calculation unit 15 calculates the sum total brightness detected by the brightness detection unit 14.

Next, the movement unit 17 relatively moves the mask A2 shown in (B) of FIG. 10 to the right in FIGS. 10 and 11 by one pixel with respect to the classification target image A1, the first image A3, and the second image A4. The brightness detection unit 14 detects the brightness of pixels of a part (28 pixels in height×2 pixels in width) of the classification target image A1 overlapping with the mask A2. The sum total brightness calculation unit 15 calculates the sum total brightness detected by the brightness detection unit 14.

Next, the movement unit 17 relatively moves the mask A2 shown in (B) of FIG. 10 to the right in FIGS. 10 and 11 by one pixel with respect to the classification target image A1, the first image A3, and the second image A4. The brightness detection unit 14 detects the brightness of pixels of a part (28 pixels in height×3 pixels in width) of the classification target image A1 overlapping with the mask A2. The sum total brightness calculation unit 15 calculates the sum total brightness detected by the brightness detection unit 14.

The movement unit 17 relatively moves the mask A2 shown in (B) of FIG. 10 to the right in FIGS. 10 and 11 one pixel at a time with respect to the classification target image A1, the first image A3, and the second image A4 until a right end portion of the classification target image A1 and the left end portion of the mask A2 are in a state of overlapping each other by one pixel. Every time the movement unit 17 relatively moves the mask A2 shown in (B) of FIG. 10 by one pixel, the brightness detection unit 14 detects the brightness of pixels in a part of the classification target image A1 overlapping with the mask A2, and the sum total brightness calculation unit 15 calculates the sum total brightness detected by the brightness detection unit 14.

In the examples shown in FIGS. 10 and 11, until calculation of the sum total brightness by the sum total brightness calculation unit 15 is completed, relative movements of the mask A2 by the movement unit 17 are performed 126 times (126 pixels) from the state shown in (A) of FIG. 11. As a result, calculation of the sum total brightness by the sum total brightness calculation unit 15 is performed 127 times.

In the examples shown in FIGS. 10 and 11, as described above, the size (100 pixels) of the mask A2 in a moving direction (transverse direction in FIGS. 10 and 11) is larger than the size (28 pixels) of the classification target image A1 in the moving direction. In addition, the size (99 pixels) of the first image A3 in the moving direction is smaller than the size (100 pixels) of the mask A2 in the moving direction by one pixel. Similarly, the size (99 pixels) of the second image A4 in the moving direction is smaller than the size (100 pixels) of the mask A2 in the moving direction by one pixel.

In the examples shown in FIGS. 10 and 11, next, the mask pattern optimization unit 18 performs machine learning and optimizes the mask pattern of the mask A2 on the basis of the sum total brightness calculated by the sum total brightness calculation unit 15. As a result, the mask A2 having the mask pattern shown in (C) of FIG. 10 is generated.

Specifically, in the examples shown in FIGS. 10 and 11, a binary convolutional neural network (CNN) is used as a machine learning algorithm. In addition, each convolutional weight of the binary convolutional neural network used by the mask pattern optimization unit 18 is either "+1" or "−1". In the example shown in (C) of FIG. 10, the dark part of the mask A2 indicates the convolutional weight "−1", and the bright part of the mask A2 indicates the convolutional weight "+1".

In another example, an arbitrary machine learning algorithm other than a binary convolutional neural network may be used as a machine learning algorithm.

Figure 12:
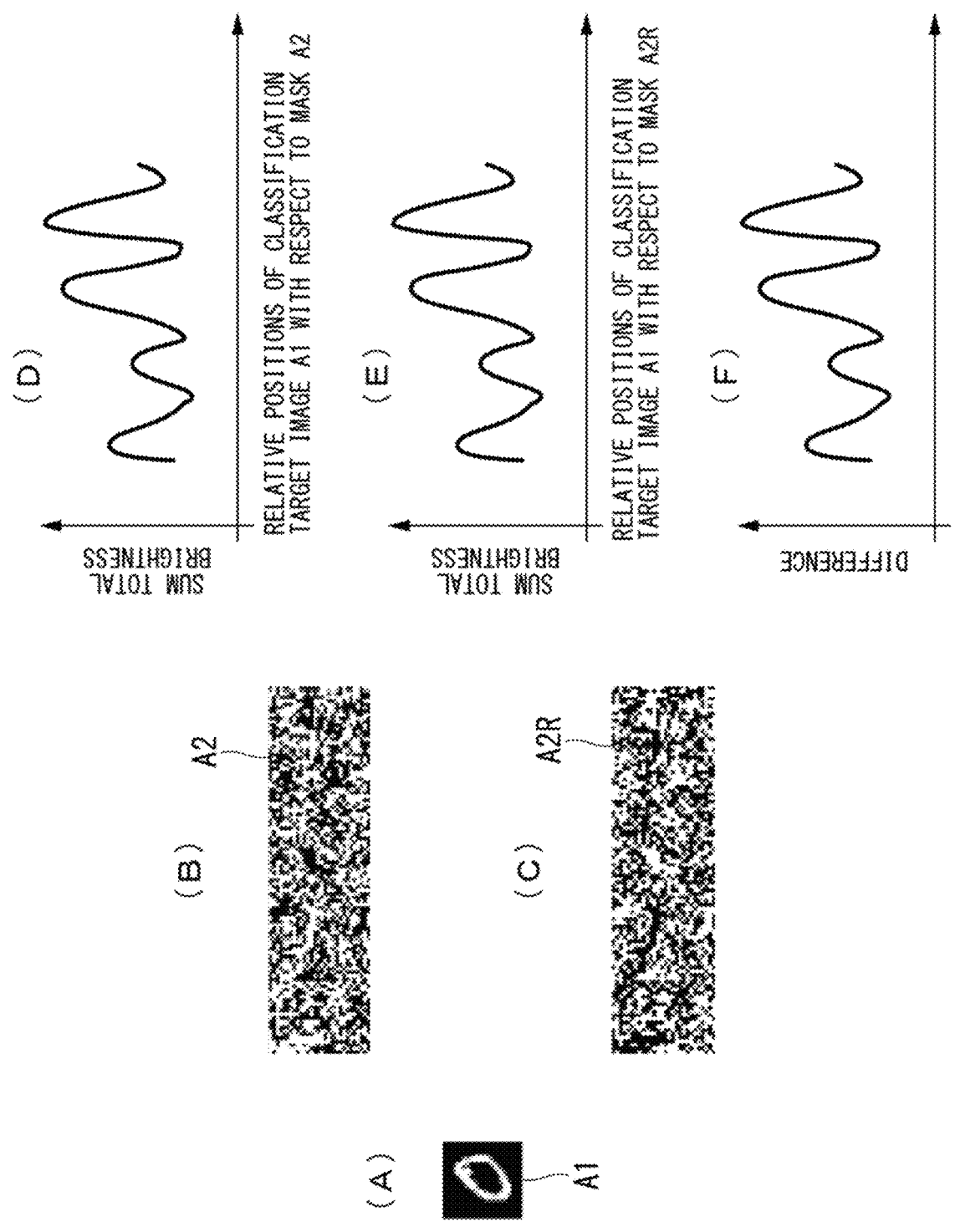
FIG. 12 is a drawing showing a way of waveform conversion using a mask of which a mask pattern is optimized by a mask pattern optimization unit.

FIG. 12 is a drawing showing a way of waveform conversion using the mask A2 of which a mask pattern is optimized by the mask pattern optimization unit 18.

Specifically, (A) of FIG. 12 is a drawing showing the classification target image A1 used in the example shown in FIG. 12. (B) of FIG. 12 is a drawing showing the mask A2 of which the mask pattern is optimized by the mask pattern optimization unit 18. (C) of FIG. 12 is a drawing showing a different mask A2R of which a mask pattern is optimized by the mask pattern optimization unit 18.

(D) of FIG. 12 is a drawing showing a waveform of the sum total brightness calculated by the sum total brightness calculation unit 15 when the mask A2 shown in (B) of FIG. 12 is applied to the classification target image A1 shown in (A) of FIG. 12. (E) of FIG. 12 is a drawing showing a waveform of the sum total brightness calculated by the sum total brightness calculation unit 15 when the mask A2R shown in (C) of FIG. 12 is applied to the classification target image A1 shown in (A) of FIG. 12. (F) of FIG. 12 is a drawing showing a difference between the waveform of the sum total brightness shown in (D) of FIG. 12 and the waveform of the sum total brightness shown in (E) of FIG. 12.

In the example shown in FIG. 12, the mask A2R shown in (C) of FIG. 12 is realized by performing black/white reverse processing of the mask A2 shown in (B) of FIG. 12. Specifically, the bright part of the mask A2 shown in (B) of FIG. 12 corresponds to the convolutional weight "+1" in the binary convolutional neural network described above. The bright part of the mask A2R shown in (C) of FIG. 12 corresponds to the convolutional weight "−1".

That is, the inventors have found through their research that the classification accuracy is improved when a mask having an optimized mask pattern is used compared to when a mask having a mask pattern set on the basis of a Bernoulli distribution is used.

In addition, the inventors have found through their research that the classification accuracy is further improved when a mask has a larger crosswise dimension.

Figure 13:
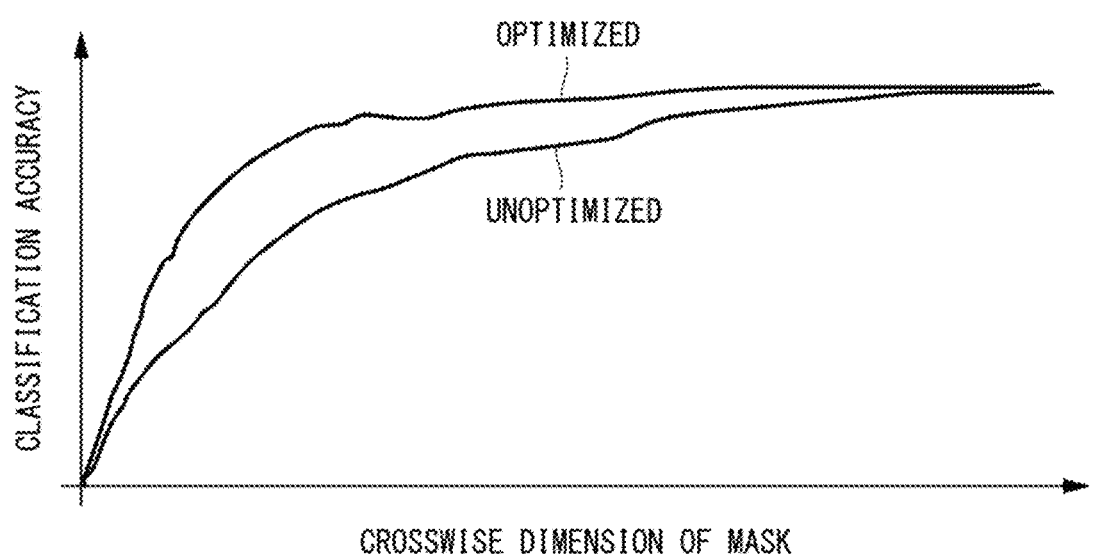
FIG. 13 is a drawing showing a hypothesis on research results assumed to be brought about by the present invention.

FIG. 13 is a drawing showing a hypothesis on results of research assumed to be brought about by the present invention. Specifically, the horizontal axis in FIG. 13 indicates the crosswise dimension of a mask. The vertical axis in FIG. 13 indicates the classification accuracy. In FIG. 13, the term "optimized" indicates a relationship between the crosswise dimension of the mask and the classification accuracy in a case in which a mask having an optimized mask pattern is used. The term "unoptimized" indicates a relationship between the crosswise dimension of the mask and the classification accuracy in a case in which a mask having a mask pattern set on the basis of a Bernoulli distribution is used.

As shown in FIG. 13, the classification accuracy in a case in which a mask having an optimized mask pattern is used becomes higher than the classification accuracy in a case in which a mask having a mask pattern set on the basis of a Bernoulli distribution is used. In addition, the classification accuracy in a case in which a mask having a large crosswise dimension is used becomes higher than the classification accuracy in a case in which a mask having a small crosswise dimension is used.

Figure 14:
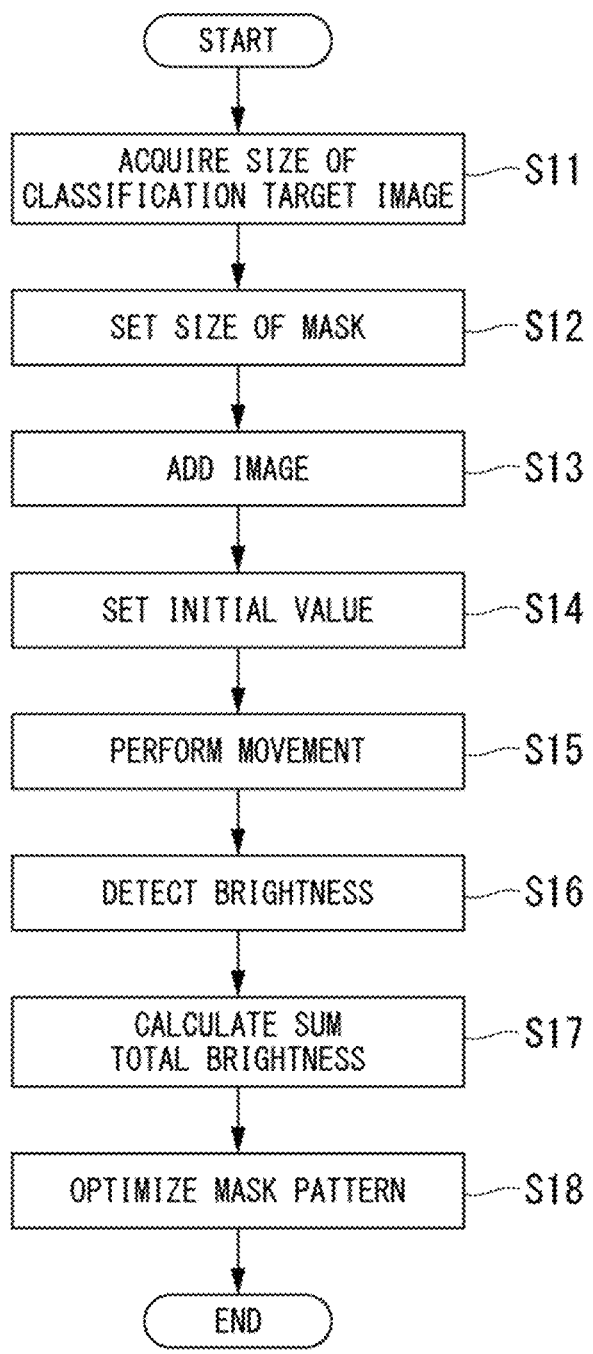
FIG. 14 is a flowchart showing an example of processing executed by the mask structure optimization device of the first embodiment.

FIG. 14 is a flowchart showing an example of processing executed by the mask structure optimization device 1 of the first embodiment.

In the example shown in FIG. 14, in Step S11, the classification target image size acquisition unit 11 acquires the size (longitudinal dimension×crosswise dimension) of the classification target image A1.

In Step S12, the mask size setting unit 12 sets the size (longitudinal dimension×crosswise dimension) of the mask A2 applied to the classification target image A1. For example, the mask size setting unit 12 causes the longitudinal dimension of the mask A2 to be identical to the longitudinal dimension of the classification target image A1 and causes the crosswise dimension of the mask A2 to be larger than the crosswise dimension of the classification target image A1.

In Step S13, the image addition unit 13 adds the first image A3 to the left side of the classification target image A1 and adds the second image A4 to the right side of the classification target image A1.

In Step S14, the initial value setting unit 16 sets the initial value for the mask pattern.

In Step S15, the movement unit 17 relatively moves the mask A2 having a mask pattern for which the initial value is set by the initial value setting unit 16 by one pixel with respect to the classification target image A1, the first image A3, and the second image A4.

In Step S16, the brightness detection unit 14 detects the brightness of each pixel in a part of the classification target image A1 overlapping with the mask A2.

In Step S17, the sum total brightness calculation unit 15 calculates the sum total brightness detected by the brightness detection unit 14.

Specifically, Steps S15 to S17 described above are executed repeatedly until the relative movements of the mask A2 with respect to the classification target image A1, the first image A3, and the second image A4 are completed.

In Step S18, the mask pattern optimization unit 18 performs machine learning and optimizes the mask pattern of the mask A2 on the basis of the sum total brightness calculated by the sum total brightness calculation unit 15.

In the example shown in FIG. 14, processing of restoring parts (that is, hidden parts) of the classification target image A1 covered by the light shielding portions A22A to A22F of the mask A2 is not performed.

In another example, processing of restoring parts of the classification target image A1 covered by the light shielding portions A22A to A22F of the mask A2 may be performed.

Application Example

The mask A2 of which the mask pattern is optimized by the mask structure optimization device 1 of the first embodiment is used in a known imaging flow sight meter, for example. Specifically, there are two kinds of flow sight meters including a cell analyzer performing only analysis of cells and a cell sorter performing fractionation in addition to analysis of cells. The mask A2 of which the mask pattern is optimized by the mask structure optimization device 1 of the first embodiment can be applied to both a cell analyzer and a cell sorter. A classification target in an application example is fine particles such as cells, for example.

Summary of First Embodiment

As described above, in the mask structure optimization device 1 of the first embodiment, the sum total brightness is calculated every time the mask A2 having a mask pattern with a set initial value is relatively moved by one pixel with respect to the classification target image A1, the first image A3, and the second image A4. In addition, the mask pattern of the mask A2 is optimized on the basis of the sum total brightness.

For this reason, according to the mask structure optimization device 1 of the first embodiment, the classification accuracy of the classification target image A1 can be improved. Specifically, for example, the classification accuracy can be improved compared to when a mask having a mask pattern set on the basis of a Bernoulli distribution is used.

Second Embodiment

Hereinafter, the mask structure optimization device 1 of a second embodiment is described.

The mask structure optimization device 1 of the second embodiment has a configuration similar to that of the mask structure optimization device 1 of the first embodiment described above except for the points which are described below. Therefore, the mask structure optimization device 1 of the second embodiment is able to produce similar results to those of the mask structure optimization device 1 of the first embodiment described above except for the points which are described below.

In the mask structure optimization device 1 of the first embodiment, as described above, each convolutional weight of the binary convolutional neural network used by the mask pattern optimization unit 18 is either "+1" or "−1".

Meanwhile, in the mask structure optimization device 1 of the second embodiment, each convolutional weight of the binary convolutional neural network used by the mask pattern optimization unit 18 is either "+1" or "0".

Moreover, the inventors have found through additional research that even if the crosswise dimension of a mask is small, the classification accuracy can be improved by executing preprocessing (which is described below) or the like with respect to the classification target image A1.

Third Embodiment

Hereinafter, the mask structure optimization device 1 of a third embodiment is described.

The mask structure optimization device 1 of the third embodiment has a configuration similar to that of the mask structure optimization device 1 of the first embodiment described above except for the points which are described below. Therefore, the mask structure optimization device 1 of the third embodiment is able to produce similar results to those of the mask structure optimization device 1 of the first embodiment described above except for the points which are described below.

Figure 15:
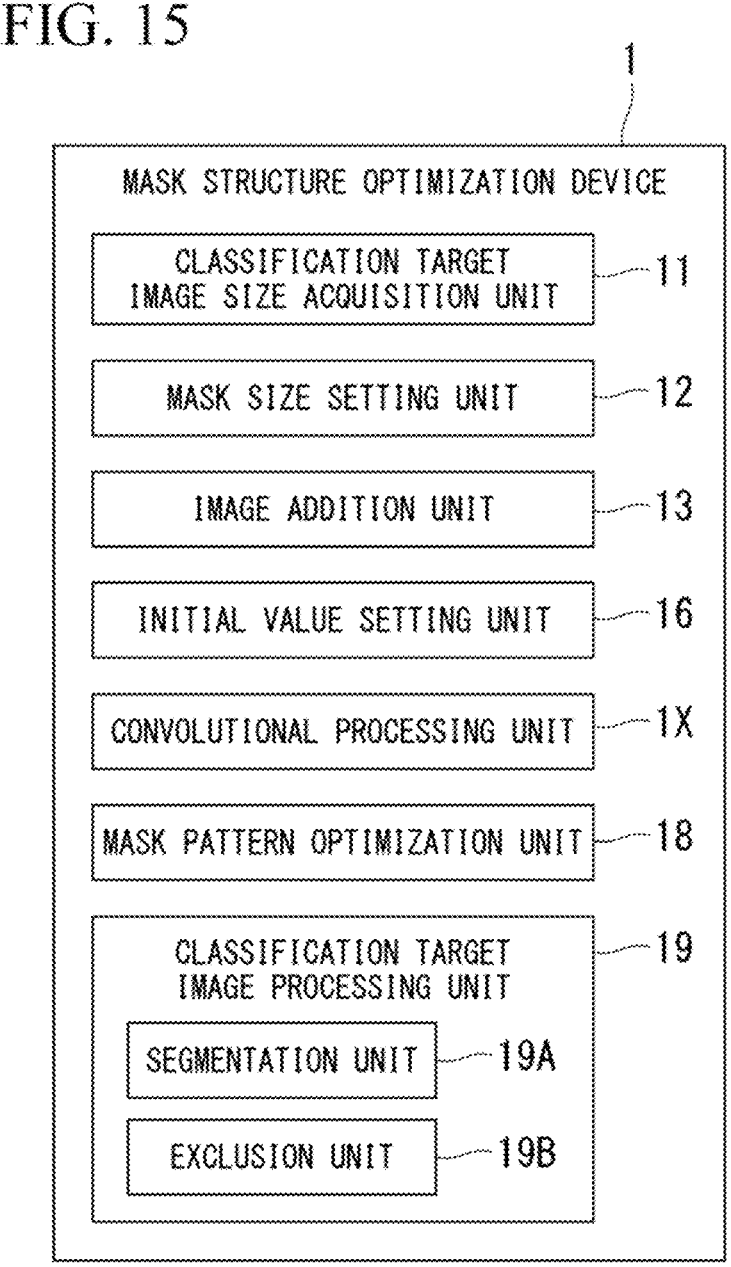
FIG. 15 is a drawing showing an example of a configuration of a mask structure optimization device of a third embodiment.

FIG. 15 is a drawing showing an example of a configuration of the mask structure optimization device 1 of the third embodiment.

In the example shown in FIG. 15, the mask structure optimization device 1 includes the classification target image size acquisition unit 11, the mask size setting unit 12, the image addition unit 13, the initial value setting unit 16, a convolutional processing unit 1X, the mask pattern optimization unit 18, and a classification target image processing unit 19.

The convolutional processing unit 1X executes convolutional processing for the classification target image A1 (refer to (A) of FIG. 2) and an image of the mask A2.

In the example shown in FIG. 15, the convolutional processing unit 1X performs fast Fourier transform (FFT) for the classification target image A1 in which the second image A4 (refer to (A) of FIG. 10) is added to the right side thereof, for example, and an image of the mask A2.

Next, the convolutional processing unit 1X multiplies the fast Fourier transformed classification target image A1 by the fast Fourier transformed image of the mask A2.

Next, the convolutional processing unit 1X performs inverse fast Fourier transform (IFFT) for a waveform obtained through multiplication processing.

Data obtained through the implementation of inverse fast Fourier transform by the convolutional processing unit 1X includes features equivalent to the sum total brightness calculated by the sum total brightness calculation unit 15 of the mask structure optimization device 1 of the first embodiment.

That is, in the mask structure optimization device 1 of the first embodiment, the mask pattern optimization unit 18 optimizes the mask pattern of the mask A2 on the basis of the sum total brightness calculated by the sum total brightness calculation unit 15. In contrast, in the mask structure optimization device 1 of the third embodiment, the mask pattern optimization unit 18 optimizes the mask pattern of the mask A2 on the basis of the results of the convolutional processing executed by the convolutional processing unit 1X (specifically, data obtained by performing inverse fast Fourier transform).

In another example (an example in which the mask A2 is known), the image A4 is not added, and the convolutional processing unit 1X performs a matrix arithmetic operation as the convolutional processing instead of fast Fourier transform. The mask pattern optimization unit 18 optimizes the mask pattern of the mask A2 on the basis of results of the matrix arithmetic operation executed by the convolutional processing unit 1X.

In the example shown in FIG. 15, the classification target image processing unit 19 executes preprocessing for the classification target image A1 (refer to (A) of FIG. 2). The classification target image processing unit 19 includes a segmentation unit 19A and an exclusion unit 19B.

The segmentation unit 19A executes processing of segmenting a plurality of classification target images from an original image including a plurality of classification targets. The exclusion unit 19B excludes a classification target image in which at least one classification target is positioned on an image outer edge portion from the plurality of classification target images segmented by the segmentation unit 19A.

Figure 16:
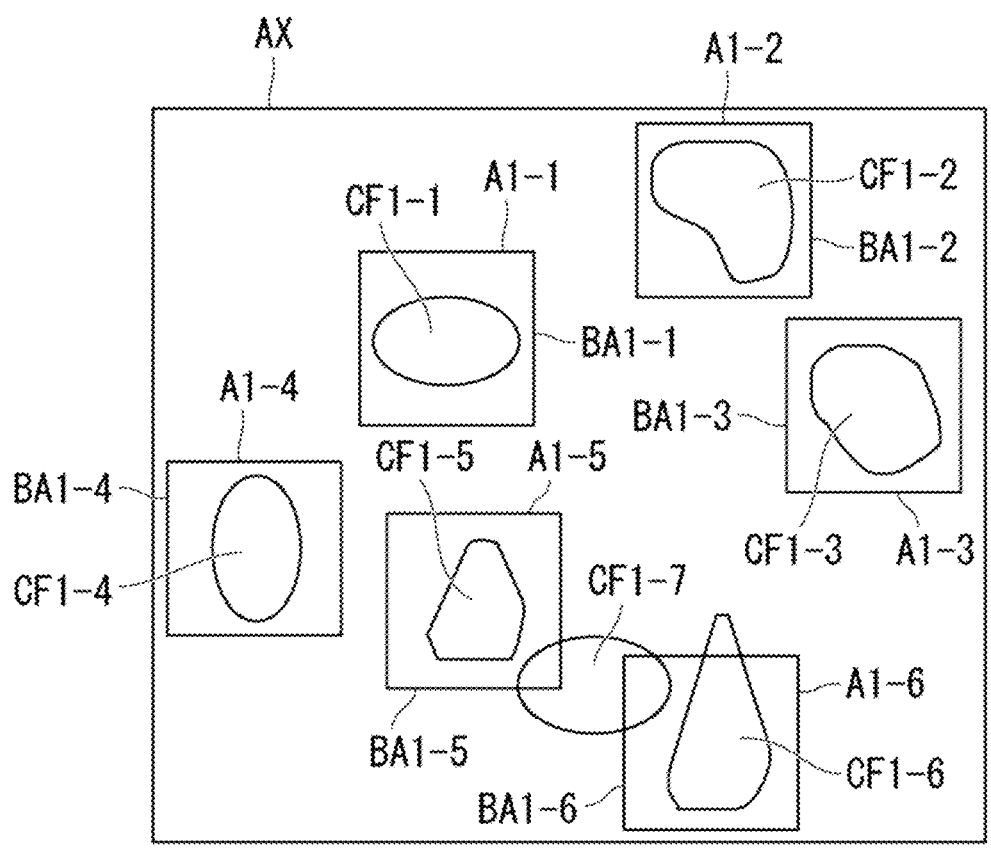
FIG. 16 is a drawing showing an example of processing performed by a segmentation unit and an exclusion unit.

FIG. 16 is a drawing showing an example of processing performed by the segmentation unit 19A and the exclusion unit 19B.

In the example shown in FIG. 16, the segmentation unit 19A segments, for example, six classification target images A1-1, A1-2, A1-3, A1-4, A1-5, and A1-6 from an original image AX including, for example, seven classification targets CF1-1, CF1-2, CF1-3, CF1-4, CF1-5, CF1-6, and CF1-7. For example, the segmentation unit 19A executes segmentation of the classification target image A1-1 such that the center of gravity of the classification target CF1-1 is positioned at the center of the classification target image A1-1.

One classification target CF1-1 is included in the classification target image A1-1 segmented by the segmentation unit 19A. The classification target CF1-1 is not positioned on an image outer edge portion BA1-1 of the classification target image A1-1. That is, the entire classification target CF1-1 is included in the classification target image A1-1.

One classification target CF1-2 is included in the classification target image A1-2 segmented by the segmentation unit 19A. The classification target CF1-2 is not positioned on an image outer edge portion BA1-2 of the classification target image A1-2. That is, the entire classification target CF1-2 is included in the classification target image A1-2.

One classification target CF1-3 is included in the classification target image A1-3 segmented by the segmentation unit 19A. The classification target CF1-3 is not positioned on an image outer edge portion BA1-3 of the classification target image A1-3. That is, the entire classification target CF1-3 is included in the classification target image A1-3.

One classification target CF1-4 is included in the classification target image A1-4 segmented by the segmentation unit 19A. The classification target CF1-4 is not positioned on an image outer edge portion BA1-4 of the classification target image A1-4. That is, the entire classification target CF1-4 is included in the classification target image A1-4.

Meanwhile, the classification target CF1-5 and a part of the classification target CF1-7 are included in the classification target image A1-5 segmented by the segmentation unit 19A. The classification target CF1-5 is not positioned on an image outer edge portion BA1-5 of the classification target image A1-5, and the classification target CF1-7 is positioned on the image outer edge portion BA1-5 of the classification target image A1-5. That is, the entire classification target CF1-5 is included in the classification target image A1-5, and a part of the classification target CF1-7 protrudes from the classification target image A1-5.

A part of the classification target CF1-6 and a part of the classification target CF1-7 are included in the classification target image A1-6 segmented by the segmentation unit 19A. The classification target CF1-6 is positioned on an image outer edge portion BA1-6 of the classification target image A1-6, and the classification target CF1-7 is also positioned on the image outer edge portion BA1-6 of the classification target image A1-6. That is, a part of the classification target CF1-6 protrudes from the classification target image A1-6, and a part of the classification target CF1-7 also protrudes from the classification target image A1-6.

Here, from the six classification target images A1-1 to A1-6 segmented by the segmentation unit 19A, the exclusion unit 19B excludes the classification target image A1-5 in which the classification target CF1-7 is positioned on the image outer edge portion BA1-5 and the classification target image A1-6 in which the classification targets CF1-6 and CF1-7 are positioned on the image outer edge portion BA1-6.

That is, in the example shown in FIG. 16, the classification target images A1-5 and A1-6 excluded by the exclusion unit 19B are not utilized for optimization of the mask A2 (refer to (B) and (C) of FIG. 10) by the mask structure optimization device 1.

Meanwhile, the classification target images A1-1 to A1-4 which are not excluded by the exclusion unit 19B are utilized for optimization of the mask A2 by the mask structure optimization device 1.

Figure 17:
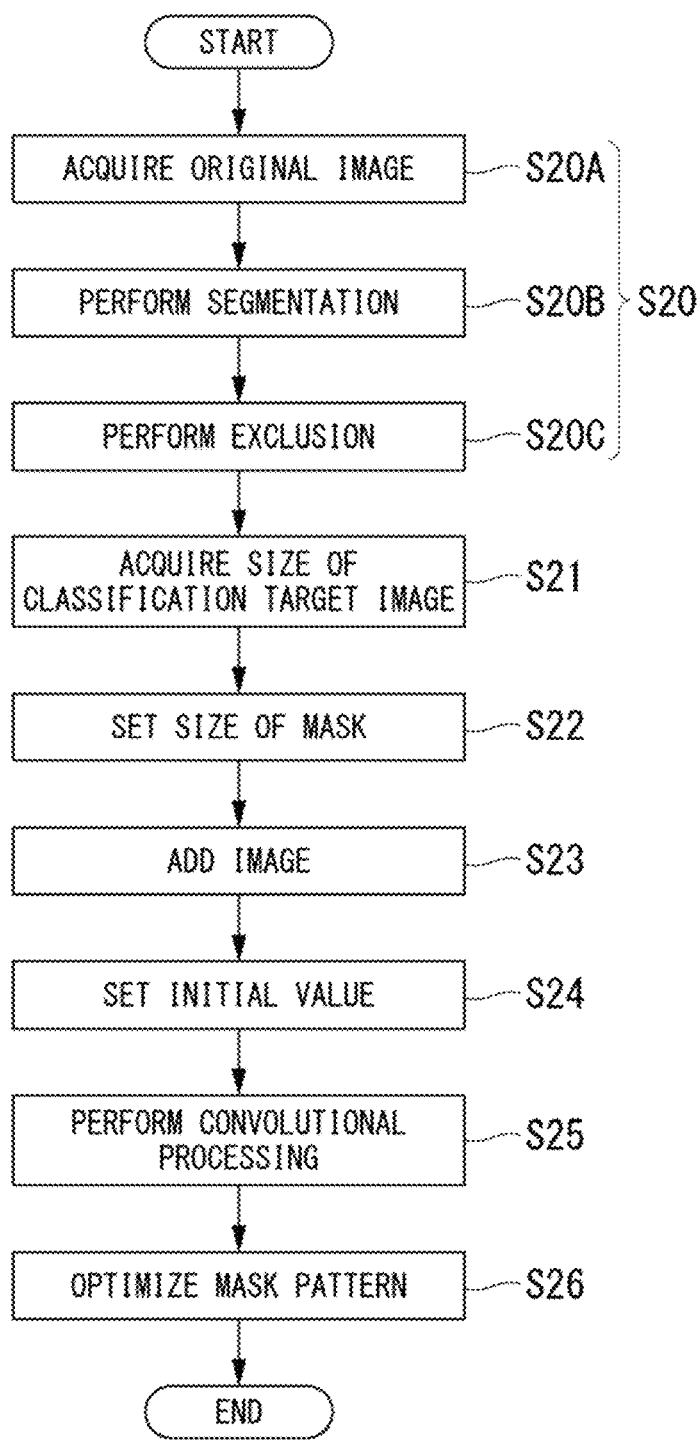
FIG. 17 is a flowchart showing an example of processing executed by the mask structure optimization device of the third embodiment.

FIG. 17 is a flowchart showing an example of processing executed by the mask structure optimization device 1 of the third embodiment.

In the example shown in FIG. 17, in Step S20, the classification target image processing unit 19 executes preprocessing for the classification target images A1-1 to A1-6 (refer to FIG. 16).

Specifically, in Step S20A, the classification target image processing unit 19 acquires the original image AX (refer to FIG. 16) including the plurality of classification targets CF1-1 to CF1-7 (refer to FIG. 16).

Next, in Step S20B, the segmentation unit 19A executes processing of segmenting the plurality of classification target images A1-1 to A1-6 (refer to FIG. 16) from the original image AX.

Next, in Step S20C, from the plurality of classification target images A1-1 to A1-6, the exclusion unit 19B excludes the classification target images A1-5 and A1-6 in which the classification targets CF1-6 and CF1-7 are positioned on the image outer edge portions BA1-5 and BA1-6 (refer to FIG. 16).

Next, in Step S21, the classification target image size acquisition unit 11 acquires the sizes (longitudinal dimension×crosswise dimension) of the classification target images A1-1 to A1-4.

Next, in Step S22, the mask size setting unit 12 sets the size (longitudinal dimension×crosswise dimension) of the mask A2 applied to the classification target images A1-1 to A1-4. For example, the mask size setting unit 12 makes the longitudinal dimension of the mask A2 identical to the longitudinal dimensions of the classification target images A1-1 to A1-4 and makes the crosswise dimension of the mask A2 smaller than the crosswise dimensions of the classification target images A1-1 to A1-4. For example, the mask size setting unit 12 sets the crosswise dimension of the mask A2 to a value corresponding to one pixel.

Next, in Step S23, the image addition unit 13 adds the first image A3 to the left sides of the classification target images A1-1 to A1-4 and adds the second image A4 to the right sides of the classification target images A1-1 to A1-4.

Next, in Step S24, the initial value setting unit 16 sets the initial value for the mask pattern.

Next, in Step S25, the convolutional processing unit 1X executes convolutional processing for the classification target image A1-1 and an image of the mask A2.

In addition, Step S25 described above is also executed for each of the classification target images A1-2, A1-3, and A1-4.

Next, in Step S26, the mask pattern optimization unit 18 performs machine learning and optimizes the mask pattern of the mask A2 on the basis of results of the convolutional processing executed in Step S25.

In the example shown in FIG. 17, Step S20 is executed before Step S21 is executed. However, in another example, Step S20 may be executed at an arbitrary timing before Step S25 is executed.

In the examples shown in FIGS. 8 to 12 described above, in order to execute optimization of the mask pattern of the mask A2, data of an MNIST is used as a classification target. However, in the examples shown in FIGS. 15 to 17, in order to execute optimization of the mask pattern of the mask A2, cells (specifically, HeLa cells (732 pieces of data) and human pancreatic cancer cells (830 pieces of data)) are used as classification targets.

Moreover, the inventors have found through additional research that optimization of the mask A2 can be executed and the classification accuracy of the classification targets using the mask A2 becomes sufficiently high by utilizing the central portion of the classification target image A1-4 even if the peripheral edge portion (that is, a part close to the image outer edge portion) of the classification target image A1-4 is not utilized, when optimization of the mask A2 (refer to (B) and (C) of FIG. 10) is executed by utilizing the classification target images A1-4 (refer to FIG. 16), for example.

In order to check the identity of an image, the classification scores are calculated by machine learning in which two-dimensional array expression of the image is arranged to be in a one-dimensional array. On the basis of the classification scores, the inventors have found through their research that when the optimized mask A2 of which the crosswise dimension corresponds to one pixel is used, achieved classification accuracy using a two-layer neural network becomes equivalent to the classification accuracy obtained by the above mentioned machine learning, that is, optimization of the mask pattern is achieved appropriately.

The classification accuracy of the classification target using the mask A2 optimized by the mask structure optimization device 1 of the third embodiment becomes higher than the classification accuracy of the classification target using a mask which is not optimized by the mask structure optimization device 1.

In addition, the classification accuracy of the classification target using the mask A2 which is optimized by the mask structure optimization device 1 of the third embodiment and of which the crosswise dimension is one pixel becomes higher than the classification accuracy of the classification target using a mask which is not optimized by the mask structure optimization device 1 and of which the crosswise dimension is 581 pixels.

Moreover, the inventors have found through additional research that the classification accuracy of the classification target using the mask A2 becomes higher when optimization of the mask A2 is executed utilizing the classification target image A1-4 (refer to FIG. 16), for example, if post-perturbation classification target images A1-4C and A1-4D (refer to FIG. 19) are generated from the classification target image A1-4 and if optimization of the mask A2 is executed utilizing the classification target image A1-4 and the post-perturbation classification target images A1-4C and A1-4D.

Fourth Embodiment

Hereinafter, the mask structure optimization device 1 of a fourth embodiment is described.

The mask structure optimization device 1 of the fourth embodiment has a configuration similar to that of the mask structure optimization device 1 of the third embodiment described above except for the points which are described below. Therefore, the mask structure optimization device 1 of the fourth embodiment is able to produce similar results to those of the mask structure optimization device 1 of the third embodiment described above except for the points which are described below.

Figure 18:
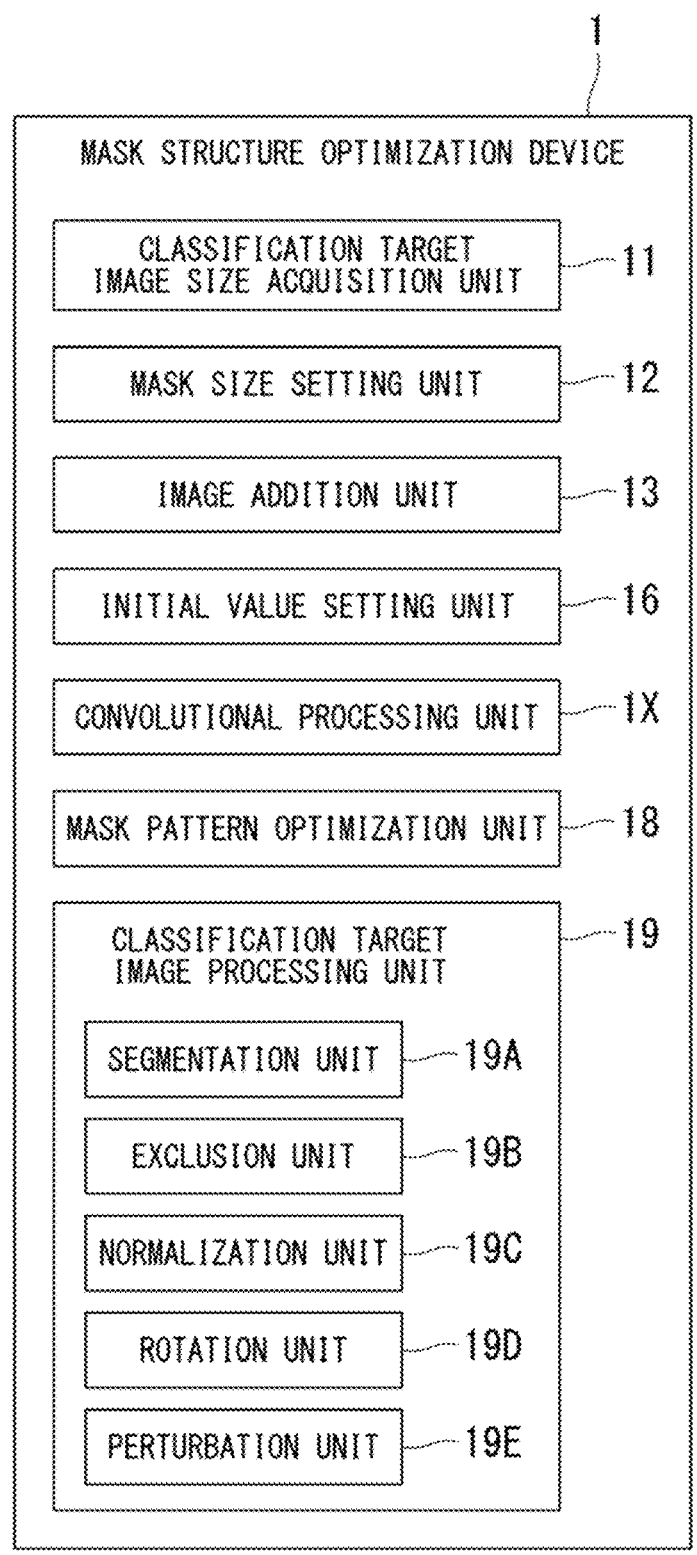
FIG. 18 is a drawing showing an example of a configuration of a mask structure optimization device of a fourth embodiment.
Figure 19:
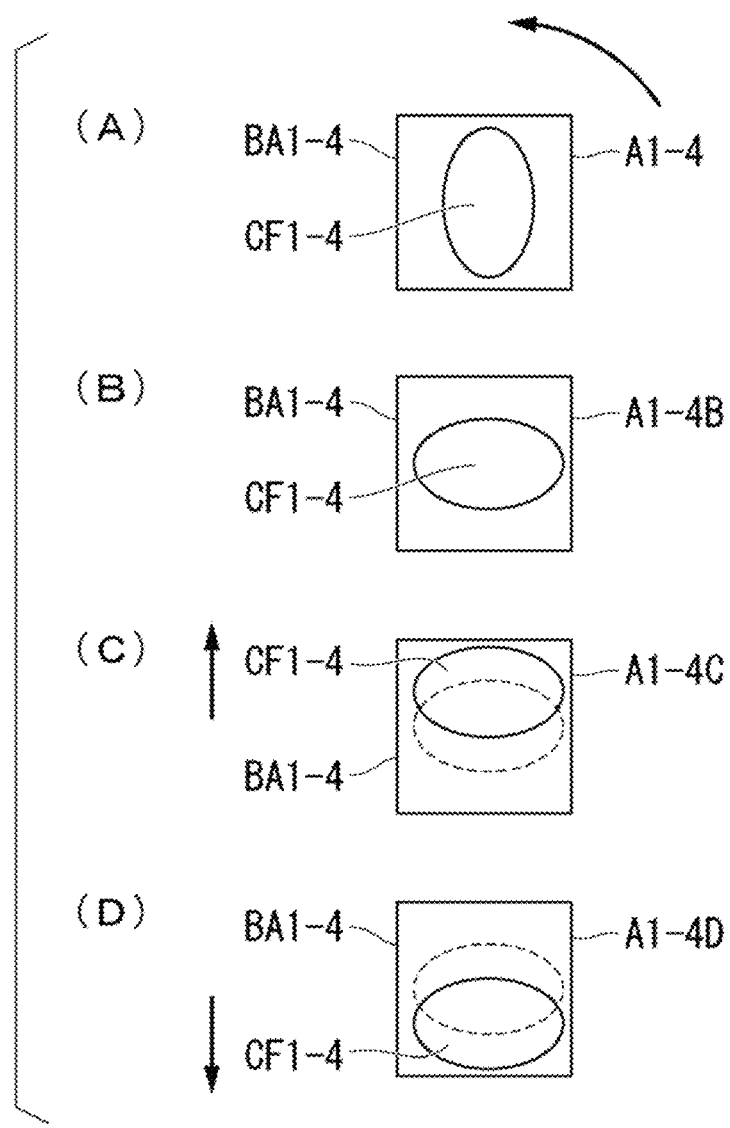
FIG. 19 is a drawing showing an example of processing performed by a rotation unit and a perturbation unit.

FIG. 18 is a drawing showing an example of a configuration of the mask structure optimization device 1 of the fourth embodiment. FIG. 19 is a drawing showing an example of processing performed by a rotation unit 19D and a perturbation unit 19E.

Figure 20:
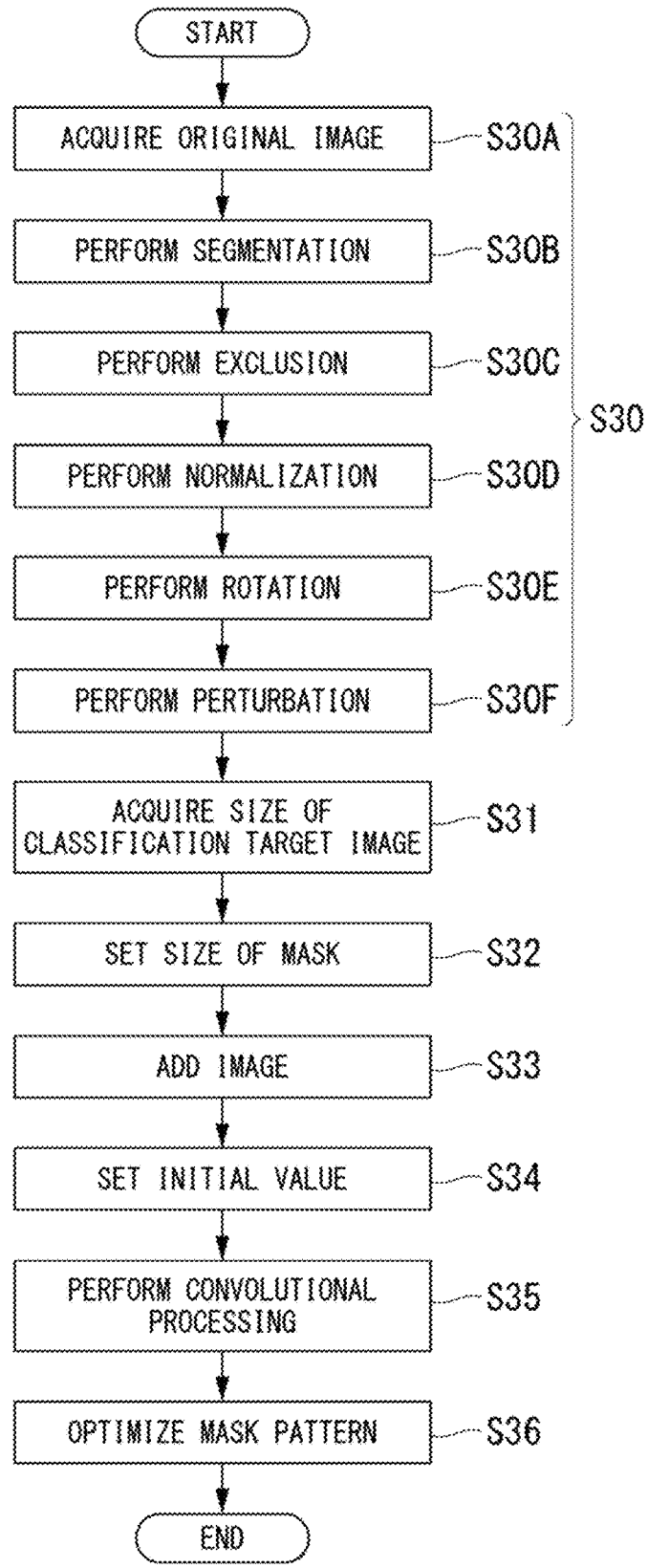
FIG. 20 is a flowchart showing an example of processing executed by the mask structure optimization device of the fourth embodiment.

In the examples shown in FIGS. 20 and 21, the classification target image processing unit 19 includes a normalization unit 19C, the rotation unit 19D, and the perturbation unit 19E, in addition to the segmentation unit 19A and the exclusion unit 19B.

The normalization unit 19C changes the pixel value of the classification target image A1 within a range of 0 to 1.

The rotation unit 19D executes processing of rotating the classification target image A1-4 (refer to (A) of FIG. 19) by 90° after processing is executed by the exclusion unit 19B and generates a post-rotation classification target image A1-4B (refer to (B) of FIG. 19).

The perturbation unit 19E executes perturbation processing for the post-rotation classification target image A1-4B after processing is executed by the exclusion unit 19B and processing is subsequently executed by the rotation unit 19D.

Specifically, the perturbation unit 19E generates the post-perturbation classification target images A1-4C and A1-4D (refer to (C) and (D) of FIG. 19) which are classification target images in which a position of the classification target CF1-4 included in the post-rotation classification target image A1-4B is moved by −5 pixels to +5 pixels in a direction (up-down direction in (B), (C), and (D) of FIG. 19) perpendicular to the moving direction without moving the position of the image outer edge portion BA1-4 of the post-rotation classification target image A1-4B, from the post-rotation classification target image A1-4B after processing is executed by the exclusion unit 19B and processing is subsequently executed by the rotation unit 19D.

In the example shown in (C) of FIG. 19, the perturbation unit 19E generates a post-perturbation classification target image A1-4C in which the position of the classification target CF1-4 included in the post-rotation classification target image A1-4B is moved in a direction (up-down direction in (C) of FIG. 19) perpendicular to the moving direction by +5 pixels.

In the example shown in (D) of FIG. 19, the perturbation unit 19E generates a post-perturbation classification target image A1-4D in which the position of the classification target CF1-4 included in the post-rotation classification target image A1-4B is moved in a direction (up-down direction in (D) of FIG. 19) perpendicular to the moving direction by −5 pixels.

In the example shown in FIG. 19, not only the post-rotation classification target image A1-4B (refer to (B) of FIG. 19) is utilized for optimization of the mask A2 by the mask structure optimization device 1, but also the post-perturbation classification target images A1-4C and A1-4D (refer to (C) and (D) of FIG. 19) are utilized for optimization of the mask A2.

In the example shown in FIG. 18, the classification target image processing unit 19 includes the rotation unit 19D. However, in another example, the classification target image processing unit 19 does not have to include the rotation unit 19D.

FIG. 20 is a flowchart showing an example of processing executed by the mask structure optimization device 1 of the fourth embodiment.

In the example shown in FIG. 20, in Step S30, the classification target image processing unit 19 executes pre-processing for the classification target images A1-1 to A1-6 (refer to FIG. 16).

Specifically, in Step S30A, the classification target image processing unit 19 acquires the original image AX (refer to FIG. 16) including the plurality of classification targets CF1-1 to CF1-7 (refer to FIG. 16).

Next, in Step S30B, the segmentation unit 19A executes processing of segmenting the plurality of classification target images A1-1 to A1-6 (refer to FIG. 16) from the original image AX.

Next, in Step S30C, the normalization unit 19C changes the pixel values of the classification target images A1-1 to A1-6 within a range of 0 to 1.

Next, in Step S30D, the exclusion unit 19B excludes the classification target images A1-5 and A1-6, in which the classification targets CF1-6 and CF1-7 are positioned on the image outer edge portions BA1-5 and BA1-6 (refer to FIG. 16), from the plurality of classification target images A1-1 to A1-6.

Next, in Step S30E, the rotation unit 19D randomly selects any angle of 0°, 90°, 180° and 270°, rotates the plurality of classification target images A1-1 to A1-4 which are not excluded by the exclusion unit 19B by the selected angle, and generates a plurality of post-rotation classification target images A1-4B and so on (refer to (B) of FIG. 19).

Next, in Step S30F, the perturbation unit 19E generates a plurality of post-perturbation classification target images A1-4C, A1-4D, and so on (refer to (C) and (D) of FIG. 19) from a plurality of post-rotation classification target images A1-4B and so on.

Next, in Step S31, the classification target image size acquisition unit 11 acquires the sizes (longitudinal dimension×crosswise dimension after rotation) of the classification target images A1-1 to A1-4.

Next, in Step S32, the mask size setting unit 12 sets the sizes (longitudinal dimension×crosswise dimension) of the mask A2 applied to the classification target images A1-1 to A1-4. For example, the mask size setting unit 12 makes the longitudinal dimension of the mask A2 identical to the longitudinal dimensions of the classification target images A1-1 to A1-4 after rotation and makes the crosswise dimension of the mask A2 smaller than the crosswise dimensions of the classification target images A1-1 to A1-4 after rotation. For example, the mask size setting unit 12 sets the crosswise dimension of the mask A2 to a value corresponding to one pixel.

Next, in Step S33, the image addition unit 13 adds the first image A3 to the left sides of the classification target images A1-1 to A1-4 and adds the second image A4 to the right sides of the classification target images A1-1 to A1-4.

Next, in Step S34, the initial value setting unit 16 sets the initial value for the mask pattern.

Next, in Step S35, the convolutional processing unit 1X executes convolutional processing for the classification target image A1-1 and an image of the mask A2.

In addition, Step S35 described above is also executed for each of the classification target images A1-2, A1-3, and A1-4.

Next, in Step S36, the mask pattern optimization unit 18 performs machine learning and optimizes the mask pattern of the mask A2 on the basis of results of the convolutional processing executed in Step S35.

Specifically, in Step S36, the mask pattern optimization unit 18 suitably executes rotation equivalent to the rotation in Step S30E and suitably executes perturbation equivalent to the perturbation in Step S30F.

In the example shown in FIG. 20, Step S30 is executed before Step S31 is executed. However, in another example, Step S30 may be executed at an arbitrary timing before Step S35 is executed.

In addition, in the example shown in FIG. 20, Step S30E is executed. However, in another example, Step S30E does not have to be executed.

The classification accuracy of the classification target using the mask A2 optimized by the mask structure optimization device 1 of the fourth embodiment becomes higher than the best value and the mean value of the classification accuracy of the classification target using a mask which is not optimized by the mask structure optimization device 1.

The processing may be performed by recording a program for realizing the functions of each of the devices according to the embodiments described above (for example, the mask structure optimization device 1) in a computer readable recording medium (storage medium) and causing a computer system to read and execute the program recorded in this recording medium.

The aforementioned "computer system" may include an operating system (OS) or hardware such as peripheral equipment.

In addition, "a computer readable recording medium" indicates a flexible disk, a magneto-optical disc, a read only memory (ROM), a writable nonvolatile memory such as a flash memory, a portable medium such as a digital versatile disc (DVD), or a storage device such as a hard disk built into the computer system. In addition, regarding a recording medium, for example, a recording medium temporarily recording data may be adopted.

Moreover, "a computer readable recording medium" also includes mediums which can retain a program for a certain period of time, for example, a server in a case in which a program is transmitted through a communication channel such as a network like the internet or a telephone channel, and a volatile memory (for example, a dynamic random access memory (DRAM)) inside a computer system serving as a client.

In addition, the foregoing program may be transmitted to a different computer system from the computer system storing this program in a storage device or the like via a transmission medium or through transmission waves in the transmission medium. Here, "a transmission medium" transmitting a program indicates a medium having a function of transmitting information, for example, a network (communication network) such as the internet, or a communication channel (communication line) such as a telephone channel.

In addition, the foregoing program may be a program for realizing some of the functions described above. Moreover, the foregoing program may be a program capable of realizing the functions described above in a combination with a program which has already been recorded in a computer system, that is, a so-called differential file (differential program).

In the computer, for example, a processor such as a central processing unit (CPU) reads and executes a program stored in a memory.

Hereinabove, the embodiments of the present invention have been described in detail with reference to the drawings. However, the specific configurations are not limited to the embodiments, and various modifications and replacements can be added within a range not departing from the gist of the present invention. The configurations disclosed in the foregoing embodiments may be combined.

REFERENCE SIGNS LIST

1 Mask structure optimization device
11 Classification target image size acquisition unit
12 Mask size setting unit
13 Image addition unit
14 Brightness detection unit
15 Sum total brightness calculation unit
16 Initial value setting unit
17 Movement unit
18 Mask pattern optimization unit
19 Classification target image processing unit
19A Segmentation unit
19B Exclusion unit
19C Normalization unit
19D Rotation unit
19E Perturbation unit
1X Convolution processing unit
A1 Classification target image
A11, A12, A13, A14 Corner portion
P1, P2, P3 Position
A2 Mask
A2R Mask
A21A, A21B, A21C Light transmitting portion
A22A, A22B, A22C, A22D, A22E, A22F Light shielding portion
A3 First image
A4 Second image

What is claimed is:

1. A mask structure optimization device comprising:
   a classification target image size acquisition unit that is configured to acquire a size of a classification target image which is an image including a classification target; a mask size setting unit that is configured to set a size of a mask applied to the classification target image;
   an initial value setting unit that is configured to set an initial value for a mask pattern of the mask;
   a convolutional processing unit that is configured to execute convolutional processing for the classification target image and an image of the mask; and
   a mask pattern optimization unit that is configured to optimize the mask pattern of the mask on the basis of results of the convolutional processing executed by the convolutional processing unit,
   wherein the mask is an optical mask having a plurality of regions with different optical characteristics.

2. The mask structure optimization device according to claim 1, further comprising:
   a classification target image processing unit that is configured to execute preprocessing for the classification target image,
   wherein the classification target image processing unit includes a segmentation unit that is configured to execute processing of segmenting a plurality of classification target images from an original image including a plurality of classification targets,
   wherein at least one classification target is included in each classification target image segmented by the segmentation unit, and
   wherein the classification target image processing unit further includes an exclusion unit that is configured to exclude a classification target image in which at least one classification target is positioned on an image outer edge portion from the plurality of classification target images segmented by the segmentation unit.

3. The mask structure optimization device according to claim 2,
   wherein the classification target image processing unit further includes a perturbation unit that is configured to execute perturbation processing for each classification target image after processing is executed by the exclusion unit, and
   wherein the perturbation unit generates a post-perturbation classification target image that is a classification target image in which a position of the one classification target included in each classification target image is moved from each classification target image after processing is executed by the exclusion unit without moving a position of the image outer edge portion of each classification target image.

4. The mask structure optimization device according to claim 1,
   wherein the classification target image and the mask have a rectangular shape, and wherein a dimension of a short side of the mask is smaller than a dimension of a long side of the classification target image and a dimension of a short side of the classification target image.

5. The mask structure optimization device according to claim 1, further comprising:

an image addition unit that is configured to add a first dark image to one side of the classification target image and is configured to add a second dark image to the other side of the classification target image.

6. The mask structure optimization device according to claim 1, wherein the mask has light transmitting portions and light shielding portions.

7. A mask structure optimization method comprising:

a classification target image size acquiring step of acquiring a size of a classification target image which is an image including a classification target;

a mask size setting step of setting a size of a mask applied to the classification target image;

an initial value setting step of setting an initial value for a mask pattern of the mask;

a convolutional processing step of executing convolutional processing for the classification target image and an image of the mask; and a mask pattern optimizing step of optimizing the mask pattern of the mask on the basis of results of the convolutional processing executed in the convolutional processing step, wherein the mask is an optical mask having a plurality of regions with different optical characteristics.

8. A computer product comprising a non-transitory computer-readable medium having recorded thereon computer-executable instructions which upon execution by a computer control:

a classification target image size acquiring step of acquiring a size of a classification target image which is an image including a classification target, a mask size setting step of setting a size of a mask applied to the classification target image, an initial value setting step of setting an initial value for a mask pattern of the mask, a convolutional processing step of executing convolutional processing for the classification target image and an image of the mask, and a mask pattern optimizing step of optimizing the mask pattern of the mask on the basis of results of the convolutional processing executed in the convolutional processing step, wherein the mask is an optical mask having a plurality of regions with different optical characteristics.

* * * * *